US006887946B2

(12) United States Patent
Fukada et al.

(10) Patent No.: US 6,887,946 B2
(45) Date of Patent: May 3, 2005

(54) (METH) ACRYLOYL GROUP-CONTAINING COMPOUND AND METHOD FOR PRODUCING THE SAME

(75) Inventors: Akihiko Fukada, Nishinomiya (JP); Keiji Yurugi, Osaka (JP); Toshio Awaji, Kawanishi (JP); Nobuaki Otsuki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 104 days.

(21) Appl. No.: 10/284,249

(22) Filed: Oct. 31, 2002

(65) Prior Publication Data

US 2003/0134926 A1 Jul. 17, 2003

(30) Foreign Application Priority Data

Nov. 1, 2001 (JP) ........................................ 2001-336860

(51) Int. Cl.[7] .............................. C09D 4/02; C08F 2/46; C08F 220/02
(52) U.S. Cl. ........................ 525/437; 525/440; 525/444; 525/445; 525/447; 524/401; 522/178; 522/179; 522/181; 522/182; 522/84; 522/71; 522/86; 522/149; 522/150; 522/154; 522/162; 522/134; 522/135; 522/137; 522/142; 522/144
(58) Field of Search ................................. 522/178, 179, 522/181, 182, 84, 71, 86, 149, 150, 154, 162, 134, 135, 137, 142, 144; 525/437, 440, 444, 445, 447; 524/401

(56) References Cited

U.S. PATENT DOCUMENTS 5,623,001 A    4/1997   Figov

FOREIGN PATENT DOCUMENTS

| JP | 63-258975 | 7/1988 |
| JP | 61-243869 | 4/1991 |
| JP | 3021755 | 10/1991 |
| JP | 3204407 | 7/1993 |
| JP | 10-306101 | 11/1998 |
| JP | 2000-186242 | 11/1999 |
| JP | 2000-63327 A | 2/2000 |
| JP | 2000-298336 | 10/2000 |
| WO | WO 02 46291 A | 6/2002 |

OTHER PUBLICATIONS

Database Caplus, Online! Chemical Abstracts Service, Columbus, Ohio, US; 1979, Database accession No. 1979:23423, XP002230590, Lapenko V.L., Prokina V.N.: "Synthesis of hydropilic ployesters of D–glucose;" abstract.
Database WPI, Week 199246, Derwent Publications Ltd., London, GB; AN 1992–378219, XP002230591 & JP 04 279609 A (Dainippon Ink), Oct. 5, 1992; abstract.
Database Caplus Online! Chemical Abstracts Service, Columbus, Ohio, US; 2000, Database accession No. 2000:356857, XP002230588 & JP 2000 144011 A (Toyo Ink) May 26, 2000; abstract.
Database Caplus Online! Chemical Abstracts Service, Columbus, Ohio,US; 2000 Shiono T. et al.Database accession No. 2000:247431, XP002230589 & JP 2000 109522 A (Toyo Ink) Apr. 18, 2000; abstract.

*Primary Examiner*—James J. Seidleck
*Assistant Examiner*—Sanza L. McClendon
(74) *Attorney, Agent, or Firm*—Sughrue Mion, PLLC

(57) ABSTRACT

It is an object of the present invention to provide a compound having a (meth)acryloyl group that is suitably used in various applications, a process for producing such compound simply and under mild conditions, and an useful photo-curable composition and aqueous photo-curable composition comprising such compound.

The present invention is related to a process for producing a compound having a (meth)acryloyl group
- which comprises reacting a compound having both a (meth)acryloyl group and a vinyl ether group with a compound having at least two functional groups capable of an addition reaction with said vinyl ether group, and to
- a compound having a (meth)acryloyl group
- which is obtained by an addition reaction of a functional group of a compound (A) having at least two functional groups and the vinyl ether group of a compound (B) having both a (meth)acryloyl group and a vinyl ether group,
- said functional groups of said compound (A) being selected from the group consisting of a hydroxyl group, a carboxyl group and a thiol group.

20 Claims, 16 Drawing Sheets

(METH) ACRYLOYL GROUP-CONTAINING COMPOUND AND METHOD FOR PRODUCING THE SAME

FIELD OF THE INVENTION

The present invention relates to a compound containing (meth)acryloyl groups and process for producing the same, and also to a photo-curable composition and an aqueous photo-curable composition that comprise the compound containing (meth)acryloyl groups.

DESCRIPTION OF THE RELATED ART (Meth)acryloyl groups containing-compounds are radical-polymerizable and therefore are useful compounds in various industrial uses. Among them, a compound having at least two (meth)acryloyl groups has a high glass transition temperature (Tg) due to an enhanced crosslinking property on curing, and thus can form a cured material excellent in physical properties such as heat resistance and the like. The compounds having at least two (meth)acryloyl groups like this are used as a polyfunctional crosslinker, a crosslinkable oligomer or a crosslinkable polymer for various uses such as matrices for composite material, casting materials, inks, coatings, paints, adhesives, various resist materials relating to electronic parts, printing plates, etc, in the fields of housing; construction and building; electric, electronic and information; transportation and so forth. Thus, the compounds having at least two (meth)acryloyl groups are required various performances according to the respective uses.

As for a process for producing a compound having at least two (meth)acryloyl groups, various processes are well known including, for example, (1) a process that comprises incorporating an alcoholic hydroxyl group and (meta)acrylic acid by dehydration reaction, (2) a process that comprises incorporating an alcoholic hydroxyl group and (meta) acryloyl chloride by dehydrochlorination, (3) a process that comprises reacting an alcoholic hydroxyl group with an isocyanate compound having a (meth)acryloyl group, and (4) a process that comprises adding glycidyl (meth)acrylate to a phenolic hydroxyl group, a carboxylic group or a thiol group by ring opening addition.

However, the conditions was hard in conventional processes for causing such problems as disappearing some (meth)acryloyl groups by polymerization and producing a colored product. In addition, the toxicity of a raw material to be used was a problem as well. Therefore, there was a room to contrive the compound having at least two (meth)acryloyl groups to be used for various uses suitably, and the process for producing the compound to be simply and effectively under mild conditions.

Incidentally, technologies for using such a compound having at least two (meth)acryloyl groups include a non-aqueous or aqueous photo-curable composition, which is used to reduce environmental damage as a mean for curing or forming an image and a pattern. A photo-curable resin composition for image-forming can be fine processed by applying the principle of photolithography and can be used to form an image by providing a cured material excellent in physical properties by photo curing, thus is utilized in various resist material relating to electronic parts and printing plates. In such a photo-curable resin composition for image-forming when photolithography is used, tack-free properties after film forming, photosensitivity during light exposure, and developability after light exposure are required. Further, when the photo-curable resin composition for image-forming is used for electronic parts as a resist material, it is required to improve water resistance and moisture resistance of the cured material, and to lower permittivity of the cured material in order to improve the transmission rate.

As this kind of photo-curable resin composition for image-forming, for example, a carboxyl group-having epoxy (meth)acrylate which is incorporated a carboxyl group by reacting epoxy(meth)acrylate, which is obtained by reacting an epoxy resin and (meth)acrylate, with an acid anhydride is used as described in Japanese Kokai publication Sho-61-243869 and Japanese Kokai publication Sho-63-258975.

However, in these techniques, a hydroxyl group of the polar group is produced in the reaction of an epoxy compound as a raw material with (meth)acrylic acid, so that there is a limit in the water resistance of the cured material and the permittivity of the cured material was difficult to be lowered. Thus, a photo-curable resin composition for image-forming having improved important properties such as water resistance and electric properties as well as satisfied reciprocal properties such as tack-free properties, photosensitivity, and developability in good balance was required. In addition, a photo-curable composition can form moldings and a pattern made of an inorganic material. As a process for forming a precise pattern from an inorganic material, there is a conventionally well known process that comprises admixing an inorganic powder such as a metal powder, a metal oxide powder, a fluorescent powder, or glass frit with a binder resin to prepare a paste-like composition, forming a pattern from this composition by photolithography method and the like, and subsequently forming a pattern by baking the organic material to thermally decompose.

As a technology for using a photo-curable binder resin, for example, Japanese Kokai publication 2000-298336 discloses an alkali-developable photo-curable composition comprising (A) an inorganic powder, (B) cellulose base carboxylic acid-modified photo-curable binder resin, (C) a photo reactive monomer, and (D) a photo polymerization initiator. In addition, Japanese Kokai publication Hei-10-306101 discloses a photo polymerizable resin composition comprising (a) a modified cellulose compound, (b) a photo polymerization initiator, (c) an ethylene compound, and (d) an inorganic and/or metallic powder.

However, in these technologies, it was required to bake the composition under comparatively high temperature conditions over a long period of time in order to remove a binder resin completely by thermal decomposition, and organic materials derived from a binder were likely to remain in inorganic moldings or an inorganic pattern which was formed by decomposition of baking organic materials, because of incomplete thermal decomposition. Thus, there was a room for further improvement in these respects. Furthermore, in pattern formation by means of photolithography method, it was also required to photocure this binder resin sufficiently in order to resolve a pattern sufficiently.

Furthermore, aqueous photo-curable compositions are expected to be used widely in a large variety of paints, adhesives, resists, and inks for printing, etc owing to the excellent curing properties of a (meth)acryloyl group having-compound due to a (meth)acryloyl group and small damage to environment because of water is used as a diluting solvent.

As for these aqueous photo-curable compositions having curing properties, for applying to ink jet field, U.S. Pat. No.

5,623,001 (columns 7 to 8) discloses an ink composition for ink jet that comprises for ink jet that comprises 20 to 75% by mass of water, a water-soluble ultraviolet-polymerizing material, a photo polymerization initiator and a coloring agent, and is capable of being cured by ultraviolet rays. Further, Japanese Patent No. 3204407 (page 1) discloses an ink for an ink jet printer that comprises at least water, a water-soluble photo-curable resin prepolymer, a photo polymerization initiator and a water-soluble dye. In addition, Japanese Kokai publication 2000-186242 (page 2 to 22) discloses an ink used for an ink jet record comprising a coloring material, a polymerizabie oligomer, water and a photopolymerizazion initiator having a solubility to water of not less than 3% by mass.

In these technologies, it is disclosed that a poly(meth)acrylate compound of polyethylene glycol is used. However, when a pigment or a dye are mixed with the (meth)acrylate compound of polyethylene glycol in water, an aggregate is formed or sedimentation is caused rapidly depending on the kind of the pigment or the dye, thereby sometimes the stability of the composition significantly deteriorates. Thus, there was a room for further improvement in these respects.

Incidentally, as to the thermosetting composition, Japanese Patent No. 3021755 discloses in pages 1, 2, 6 and 7 that an acetal group- or ketal group-containing compound, which is a homopolymer or copolymer of an adduct of vinyloxyalkyl (meth)acrylate and alcohols or ortho acid ester, can be used as the constitutional component in such acetal group- or ketal group-containing composition, an adduct is used as a intermediate for forming the homopolymer or copolymer, however, there is no disclosure about the utilization of such adduct for various paints, adhesives, resists, print ink and the like. Also, it does not disclose about setting the number of functional group in alcohols or ortho acid ester used in synthesizing the adduct, nor about setting the number of (meth)acryloyl group in the adduct.

SUMMARY OF THE INVENTION

Developed in the light of the above state of the art, the present invention has for its object to provide a compound having a (meth)acryloyl group that is suitably used in various applications, a process for producing such compound simply and under mild conditions, and an useful photo-curable composition and aqueous photo-curable composition comprising such compound.

The present inventors found that a low molecular weight compound, an oligomer and a polymer having a (meth)acryloyl group are produced simply under mild conditions without the product being colored or some (meth)acryloyl group being polymerized, when reacting a compound having both a (meth)acryloyl group and a vinyl ether group with a compound having at least two functional groups capable of an addition reaction with the vinyl ether group, among others the functional groups of the compound being selected from the group consisting of a hydroxyl group, a carboxyl group and a thiol group. Further the present inventors also found that the low molecular weight compound, the oligomer and the polymer having a (meth)acryloyl group obtained thereby are useful compounds excellent in physical properties of cured materials as a polyfunctional crosslinker, a crosslinkable oligomer or a crosslinkable polymer for various applications such as matrices for composite material, casting materials, inks, coatings, paints, adhesives, various resist materials relating to electronic parts, printing plates, etc. in the fields of housing; construction and building; electric, electronic and information; transportation and so forth. Then with these findings, it means to be able to solve the above-mentioned problems.

A composition comprising both the compound having a (meth)acryloyl group and a photo polymerization initiator is found to a photo-curable composition capable of fine image-forming, because, when photolithography is used, the composition can form a high resolution pattern, and is excellent in both developing properties and tack-free properties of a film, in addition, water resistance and moisture resistance of the cured material can be improved, and lower permittivity can be attained. Further a composition comprising an inorganic powder is found to be a photo-curable composition useful in various applications such as an electronic parts, because the composition is excellent in thermal decomposition properties during baking and is able to form moldings and a precise pattern using an inorganic material. Further, when water is contained, the composition is able to be an aqueous one, which is well in curing properties and water resistance after curing due to the reactivity of a (meth)acryloyl group and in which the decrease in dissolution stability and dispersion stability is suppressed even when coloring agents such as a dye and a pigment are coexistent. Furthermore, the composition is able to be an aqueous photo-curable composition useful suitably in various applications, because the composition is an aqueous one.

These findings have led to completion of the present invention.

The present invention thus provides a process for producing a compound having a (meth)acryloyl group which comprises reacting a compound having both a (meth)acryloyl group and a vinyl ether group with a compound having at least two functional groups capable of an addition reaction with said vinyl ether group.

The present invention also provides a photo-curable composition which comprises both the compound having a (meth)acryloyl group and a photo polymerization initiator.

The present invention also provides an aqueous photo-curable composition which comprises the compound having a (meth)acryloyl group and water.

DETAILED DESCRIPTION OF THE INVENTION

In the following, the present invention is described in detail.

The process for producing a compound having a (meth)acryloyl group of the present invention comprises a reaction of a compound having both a (meth)acryloyl group and a vinyl ether group and a compound having at least two functional groups capable of an addition reaction with the vinyl ether group. As the compound having a (meth)acryloyl group produced by the present invention, the compound having at least two (meth)acryloyl groups is preferable.

In the present invention, a compound having both a (meth)acryloyl group and a vinyl ether group and a compound having at least two functional groups capable of an addition reaction with the vinyl ether group (hereinafter, also referred to as a compound having at least two functional groups) may be used singly or in combination of two or more species.

The compound having both a (meth)acryloyl group and a vinyl ether group suitably include such as a (meth)acrylate indicated by General Formula (3) below:

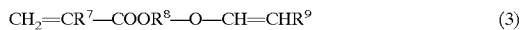

$$CH_2=CR^7-COOR^8-O-CH=CHR^9 \quad (3)$$

wherein, $R^7$ represents a hydrogen atom or a methyl group, $R^8$ an organic moiety, and $R^9$ a hydrogen atom or an organic moiety.

Suited for use as the organic moiety indicated by $R^8$ are a linear, branched or cyclic alkylene group of 2 to 18 carbon atoms, an alkoxy alkylene group of 2 to 20 carbon atoms, a halogenated (for example, chlorinated, brominated, or fluorinated)alkylene group of 2 to 8 carbon atoms, a polyethylene glycol structure except for the end hydroxyl groups, a polypropylene glycol structure except for the end hydroxyl groups, a polybutylene glycol structure except for the end hydroxyl groups and an aryl group. Among them, a polyethylene glycol structure, a polypropylene glycol structure and a polybutylene glycol structure, their degree of polymerization is 1 to 10,000, and an alkylene group of 2 to 4 carbon atoms are suited. More preferable are a polyethylene glycol structure, a polypropylene glycol structure and a polybutylene glycol structure, their degree of polymerization is 1 to 100, an alkylene group of 2 carbon atoms (—CH$_2$CH$_2$—), and an alkylene group of 3 carbon atoms (—CH$_2$CH$_2$CH$_2$—). Most preferable are a polyethylene glycol structure, a polypropylene glycol structure and a polybutylene glycol structure, their degree of polymerization is 1 to 15.

Suited for use as the organic moiety indicated by $R^9$ are a linear, branched or cyclic alkyl group of 1 to 10 carbon atoms, and an aromatic group, which may be substituted, of 6 to 11 carbon atoms. Among them, an alkyl group of 1 to 2 carbon atoms and an aromatic group of 6 to 8 carbon atoms are suited.

Specifically, compounds indicated by General Formula (3) suitably include the following species: 2-vinyloxyethyl (meth)acrylate, 3-vinyloxypropyl (meth)acrylate, 1-methyl-2-vinyloxyethyl (meth)acrylate, 2-vinyloxypropyl (meth)acrylate, 4-vinyloxybutyl (meth)acrylate, 1-methyl-3-vinyloxypropyl (meth)acrylate, 1-vinyloxymethylpropyl (meth)acrylate, 2-methyl-3-vinyloxypropyl (meth)acrylate, 1,1-dimethyl-2-vinyloxyethyl (meth)acrylate, 3-vinyloxybutyl (meth)acrylate, 1-methyl-2-vinyloxypropyl (meth)acrylate, 2-vinyloxybutyl (meth)acrylate, 4-vinyloxycyclohexyl (meth)acrylate, 6-vinyloxyhexyl (meth)acrylate, 4-vinyloxymethylcyclohexylmethyl (meth)acrylate, 3-vinyloxymethylcyclohexylmethyl (meth)acrylate, 2-vinyloxymethylcyclohexylmethyl (meth)acrylate, p-vinyloxymethylphenylmethyl (meth)acrylate, m-vinyloxymethylphenylmethyl (meth)acrylate, o-vinyloxymethylphenylmethyl (meth)acrylate, 2-(vinyloxyethoxy)ethyl (meth)acrylate, 2-(vinyloxyisopropoxy)ethyl (meth)acrylate, 2-(vinyloxyethoxy)propyl (meth)acrylate, 2-(vinyloxyethoxy)isopropyl (meth)acrylate, 2-(vinyloxyisopropoxy)propyl (meth)acrylate, 2-(vinyloxyisopropoxy)isopropyl (meth)acrylate, 2-(vinyloxyethoxyethoxy)ethyl (meth)acrylate, 2-(vinyloxyethoxyisopropoxy)ethyl (meth)acrylate, 2-(vinyloxyisopropoxyethoxy)ethyl (meth)acrylate, 2-(vinyloxyisopropoxyisopropoxy)ethyl (meth)acrylate, 2-(vinyloxyethoxyethoxy)propyl (meth)acrylate, 2-(vinyloxyethoxyisopropoxy)propyl (meth)acrylate, 2-(vinyloxyisopropoxyethoxy)propyl (meth)acrylate, 2-(vinyl oxyisopropoxyethoxy)propyl (meth)acrylate, 2-(vinyloxyethoxyethoxy)isopropyl (meth)acrylate, 2-(vinyloxyethoxyisopoxy)isopropyl (meth)acrylate, 2-(vinyloxyisopropoxyethoxy)isopropyl (meth)acrylate, 2-(vinyloxyisopropoxyisopropoxy)isopropyl (meth) acrylate, 2-(vinyloxyethoxyethoxyethoxy)ethyl (meth) acrylate, 2-(vinyloxyethoxyethoxyethoxyethoxy)ethyl (meth)acrylate, 2-(vinyloxyisopropoxyethoxy)ethyl (meth) acrylate, 2-(vinyloxyisopropoxyethoxyethoxy)ethyl (meth) acrylate, 2-(vinyloxyisopropoxyethoxyethoxyethoxy)ethyl (meth)acrylate, 2-(vinyloxyisopropoxyethoxyethoxyethoxyethoxy)ethyl (meth)acrylate, polyethylene glycol monovinyl ether (meth) acrylate, polypropylene glycol monovinyl ether (meth) acrylate, and polybutylene glycol monovinyl ether (meth) acrylate.

The above-mentioned compounds having at least two functional groups capable of an addition reaction with the vinyl ether group may be low molecular weight compounds, oligomers or polymers. The functional groups capable of an addition reaction with the vinyl ether group suitably include a hydroxyl group, a carboxyl group and a thiol group. That is, suited for use as these compounds having at least two functional groups are compounds having at least two functional groups being selected from the group consisting of a hydroxyl group, a carboxyl group and a thiol group. In this way, a (meth)acryloyl group can be incorporated under mild conditions by reacting a compound having both a (meth) acryloyl group and a vinyl ether group with a compound having at least two functional groups selected from the group consisting of a hydroxyl group, a carboxyl group and a thiol group. Thus, a compound having a (meth)acryloyl group are produced simply under mild conditions without the product being colored.

The above-mentioned compounds having at least two functional groups, among others the functional groups of the compound being selected from the group consisting of a hydroxyl group, a carboxyl group and a thiol group, suitably include the species described in (1) to (6) below:

(1) a compound having a hydroxyl group: a polyhydric alcohol such as ethylene glycol, propylene glycol, butylene glycol, 1,3-propanediol, 1,4-cyclohexanedimethanol, 1,4-cyclohexanediol, 1,4-butanediol, neopenthyl glycol, xylylene glycol, hexanediol, glycerin, polyglycerin, trimethylolpropane, pentaerythritol, dipentaerythritol, hydrogenated bisphenol A, alkylene oxide adducts of bisphenol A, polyethylene glycol, polypropylene glycol, unsaturated polyesters, saturated polyesters, epoxyacrylate, phenoxy resins, hydroxyl group-containing polymers and epoxy resins; polycondensed compounds of phenols such as bisphenol, hydroquinone, resorcinol, pyrogallol and phenol resins; p-hydroxyphenethyl alcohol; saponificated compounds of poly(vinyl alcohol)resins; cellulose; sugars such as glucose, fructose, mannite, starch, sorbitol and dextran.

(2) a compound having a carboxyl group: oxalic acid, malonic acid, succinic acid, glutaric acid, adipic acid, maleic acid, fumaric acid, phthalic acid, tetrahydrophthalic acid, hexahydrophthalic acid, dimeric acids, trimellitic acid, pyromellitic acid, butanetetracarboxylic acid, unsaturated polyesters, saturated polyesters, reaction products of epoxy resins and dibasic acids, reaction products of epoxyacrylate and dibasic acids and carboxyl group-having polymers.

(3) a compound having a thiol group: 2,3-butanediol, dipentenedithiol, ethylcycrohexyldithiol, 1,6-hexanedithiol, trimethylolpropanetris-(thioglycolate), pentaerythritoltetrakis-(thioglycolate), 1,4-butanedioldi (β-thiopropyonate), trimethylolpropanetris(β-thiopropyonate) and pentaerythritoltetrakis-(β-thiopropyonate).

(4) a compound having a hydroxyl group and a carboxyl group: hydroxy acids such as hydroxyacetic acid, lactic acid, glyceric acid, tartaric acid and citric acid; hydroxybenzoic acid, hydroxynaphthoic acid, unsaturated polyesters, saturated polyesters, and polymers having both a carboxyl group and a hydroxyl group.

(5) a compound having a hydroxyl group and a thiol group: mercaptoethanol.

(6) a compound having a carboxyl group and a thiol group: mercaptopropionic acid. Among them, epoxyacrylate, unsaturated polyesters, phenol resins, epoxy resins, phenoxy resins and hydroxyl group-containing polymers are suited.

As the above-mentioned epoxyacrylate, an epoxyacrylate having a (meth)acryloyl group can be obtained by an addition reaction of an epoxy resin such as bisphenol type and novolac type with (meth)acrylic acid. The epoxyacrylate can be obtained by an addition reaction of an epoxy resin with an unsaturated monobasic acid by ring opening. The unsaturated monobasic acid suitably include an unsaturated monobasic acid mentined later and one or two or more species can be used. Furthermore, as required, a saturated monobasic acid and/or a polybasic acid can be used in combination with an unsaturated monobasic acid.

Any well known epoxy resins having at least two epoxy groups in one molecule can be used as an epoxy resin to compose an epoxyacrylate. Suited for use as the epoxy resin are bisphenol-type epoxy resins; biphenyl-type epoxy resins; alicyclic epoxy resins; polyfunctional glycidylamine resins such as tetraglycidyldiaminodiphenylmethane; polyfunctional glycidyl ether resins such as tetraglycidyl tetraphenyl ethane; phenol novolac-type epoxy resins and cresol novolac-type epoxy resins; reaction products of epichlorohydrin and a polyphenol compound obtained by a condensation of a phenol compound such as phenol, o-cresol, m-cresol and naphthol with an aromatic aldehyde having a phenolic hydroxyl group; reaction products of epichlorohydrin and a polyphenol compound obtained by an addition reaction of a phenol compound with a diolefin compound such as divinyl benzene and dicyclopentadiene; an epoxidized compound of a ring-opened polymer of 4-vinylcyclohexene-1-oxide using a peracid; epoxy resins containing a heterocyclic ring such as triglycidylisocyanurate; phenolaralkyl-type epoxy resins. In addition, a chain-elongated compound can also be used. said chain-elongated compound is obtained by bonding of at least two of these epoxy resin molecules with a chain elongating agent such as a polybasic acid, a polyphenol compound, a polyfunctional amino compound, and polythiol. One or two or more species of them can be used.

Additionally, a high molecular weight epoxyacrylate can also be used that is prepared by partially reacting alcoholic hydroxyl groups of an epoxyacrylate with a compound such as poly-isocyanate compound, polyvinyl ether and a dianhydride of tetrabasic acid, or by reacting a carboxyl group and a compound such as a polyfunctional epoxy compound and a polyfunctional oxazoline compound, the above-mentioned carboxyl group being produced by a partial addition reaction of an acid anhydride and alcoholic hydroxyl groups of an epoxyacrylate.

Well known reaction conditions can be adopted for reaction conditions such as reaction temperature and reaction time when the above-mentioned epoxyacrylate is produced by an addition reaction of an epoxy resin with an unsaturated monobasic acid by ring opening. In other words, the process for producing an epoxyacrylate is not particularly limited.

As the above-mentioned unsaturated polyesters, a polymer containing both an ester linkage and an unsaturated double bond can be obtained by a condensation of an unsaturated dicarboxylic acid and a polyhydric alcohol. The above-mentioned unsaturated polyester is a polymer having an unsaturated bond obtained by a condensation polymerization of an acid component mainly having an unsaturated polybasic acid and a polyhydric alcohol component mainly containing a polyhydric alcohol and/or an epoxy compound.

The above-mentioned acid component may further, as required, contain a saturated polybasic acid such as an aliphatic saturated polybasic acid and an aromatic saturated polybasic acid, or may further contain a monobasic acid such as an unsaturated monobasic acid (unsaturated monocarboxylic acid) like acrylic acid, methacrylic acid, cinnamic acid and derivatives of these carboxylic acids, and a saturated monobasic acid (saturated monocarboxylic acid). The above-mentioned polyhydric alcohol component may further, as required, contain a monohydric alcohol such as hydroxydicyclopentadiene, benzyl alcohol and allyl alcohol. A monobasic acid and a monohydric alcohol are not particularly limited. Furthermore, (meth)acrylate modified unsaturated polyesters can also be used that is obtained by a ring opening addition of a glycidyl (meth)acrylate and a end carboxyl group of unsaturated polyesters.

As the above-mentioned unsaturated polybasic acids used for acid component, any compounds containing within the same molecule both at least one double bond capable of polymerization with a vinyl monomer and at least two substituent groups can be used. The above-mentioned substituent groups is substituent groups (e.g., carboxyl group) which can form an ester linkage by reacting with a functional group (namely, hydroxyl group and/or epoxy group) of a polyhydric alcohol used as a polyhydric alcohol component and/or an epoxy compound. The unsaturated polybasic acids used for acid component are not particularly limited.

Suited for use as the above-mentioned unsaturated polybasic acids are, for example, $\alpha,\beta$-unsaturated polybasic acids such as maleic acid, fumaric acid, aconitic acid and itaconic acid; $\beta,\gamma$-unsaturated polybasic acids such as dihydromuconic acid. In addition, derivatives of unsaturated polybasic acids can be used instead of unsaturated polybasic acids. The derivatives suitably include, for example, anhydrides, halides and alkylesters of the above-mentioned unsaturated polybasic acids. These unsaturated polybasic acids and derivatives may be used singly or in combination of two or more species.

Suited for use as the above-mentioned saturated polybasic acids used as an acid component when required are, for example, aliphatic saturated polybasic acids such as malonic acid, succinic acid, methylsuccinic acid, 2,2-dimethysuccinic acid, 2,3-dimethysuccinic acid, hexylsuccinic acid, glutaric acid, 2-methylglutaric acid, 3-methyiglutaric acid, 2,2-dimethylglutaric acid, 3,3-dimethylglutaric acid, 3,3-diethylglutaric acid, adipic acid, pimelic acid, suberic acid, azelaic acid, and sebasic acid; aromatic saturated polybasic acids such as phthalic acid, isophthalic acid, terephthalic acid, trimellitic acid, and pyromellitic acid; and alicyclic saturated polybasic acids such as 1,4,5,6,7,7-hexachloro-5-norbornen-2,3-dicarboxylic acid, 1,2-hexahydrophthalic acid, 1,1-cyclobutane dicarboxylic acid, 5-norbornene-2,3-dicarboxylic acid, and trans-1,4-cyclohexane dicarboxylic acid. In addition, derivatives of saturated polybasic acids can also be used instead of saturated polybasic acids. The derivatives suitably include, for example, anhydrides, halides and alkylesters of the above-mentioned saturated polybasic acids. These saturated polybasic acids and derivatives may be used singly or in combination of two or more species.

Suited for use as the above-mentioned polyhydric alcohol used as polyhydric alcohol component are, ethylene glycol, diethylene glycol, 1,3-propanediol, 2-methyl-1,3- propanediol, 1, 4-butanediol, 1, 3-butanediol, 2,3-butanediol, dipropylene glycol, 1,5-pentanediol, 1,6-hexanediol, 2,2-dimethyl-1,3-propanediol (neopenthyl glycol), 2-ethyl-1,4-butanediol, 1,7-heptanediol, 1,8-octanediol, 1,9-nonanediol, 1,10-decanediol, 1,4-cyclohexanediol, 1,4-dimethylol cyclohexane, 2,2-diethyl-1,3-propanediol, 3-methyl-1,4-pentanediol, 2,2-diethyl-1,3-butanediol, 4,5-nonanediol, triethylene glycol, glycerin, trimethylol propane, pentaerythritol, dipentaerythritol, hydrogenated bisphenol A, alkylene oxide adducts of hydrogenated bisphenol A, and alkylene oxide adducts of bisphenol A. These may be used singly or in combination of two or more species.

Epoxy compounds used as the above-mentioned polyhydric alcohol component suitably includes ethylene oxide, propylene oxide, butylene oxide, styrene oxide, a glycidyl acrylate, glycidyl methacrylate, and diglycidyl ether of bisphenol A. These may be used singly or in combination of two or more species.

The ratio between the polyhydric alcohol and the epoxy compound, when they are used in combination as the above-mentioned polyhydric alcohol component, maybe chosen according to the kinds of polyhydric alcohols and epoxy compounds, and is not particularly limited. In addition, the ratio of the above-mentioned monohydric alcohol to the polyalcohol components is preferably less than 50% by mass.

Well known reaction conditions can be adopted for reaction conditions such as reaction temperature and reaction time when the above-mentioned unsaturated polyesters is produced by a condensation polymerization of an acid component and an polyhydric alcohol component. In other words, the process for producing unsaturated polyesters is not particularly limited.

The above-mentioned phenol resins include, for example, phenol novolac, cresol novolac; copolycondensates of formaldehyde and a phenol compound such as phenol, o-cresol, m-cresol and naphtol; copolycondensates of a phenol compound such as o-cresol, m-cresol and naphtol and an aromatic aldehyde containing a phenolic hydroxyl group; polyphenols obtained by addition reaction of a phenol compound and a diolefin compound such as divinyl benzene and dicyclopentadiene; copolycondensates of xylylene glycol and a phenol compound such as phenol, o-cresol, m-cresol and naphtol; phenolbiphenyl aralkyl, phenoldiphenyl ether aralkyl, naphtolbiphenyl aralkyl, and naphtoldiphenyl ether aralkyl. These may be used singly or in combination of two or more species.

As the above-mentioned epoxy resins, any of the hydroxyl group-having epoxy resins which is used to compose the above-mentioned epoxy acrylate can be used. As the epoxy resins, for example, a chain-elongated epoxy resin can be suitably used. Said chain-elongated epoxy resin is obtained by reacting an epoxy resin having two or more functional groups such as bisphenol-type epoxy resins, phenol novolac epoxy resins and cresol novolac epoxy resins with a chain elongating agent such as a polybasic acid, a polyphenol compound, a polyfunctional amino compound, and polyfunctional thiol compound. One or two or more species of them can be used.

As the above-mentioned phenoxy resins, a polymer having both a phenoxy structure indicated by the general formula (4):

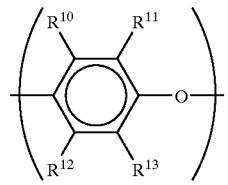

wherein $R^{10}$, $R^{11}$, $R^{12}$ and $R^{13}$ each independently represents a hydrogen atom, a halogen or an alkyl group of C1 to C5, and at least two alcoholic hydroxyl groups within the molecule can be used. The polymer can be obtained by reacting bisphenol A or tetrabromobisphenol A with a bisphenol A-type epoxy resins or a tetrabromobisphenol A-type epoxy resins.

The above-mentioned hydroxyl group-having polymers are not particularly limited if the polymer contains at least two hydroxyl groups formed by polymerizing of monomer components. Processes for incorporating a hydroxyl group are not particularly limited, and suitably include, for example, (1) a method of copolymerizing monomers containing a hydroxyl group, (2) a method that involves copolymerizing monomers containing a carboxyl group, and subsequently carrying out the addition reaction of a compound having a glycidyl group with the carboxyl group to generate a hydroxyl group, (3) a method that involves copolymerizing monomers containing a glycidyl group, and subsequently carrying out the addition reaction of a compound containing a carboxyl group with the glycidyl group to generate a hydroxyl group, and (4) a method of using a polymerization initiator or a chain transfer agent each of which contains a hydroxyl group. These methods can be used singly or in combination of two or more methods. The above-mentioned monomer components are not particularly limited, and include (meth)acrylates such as methyl (meth) acrylate, ethyl (meth)acrylate, butyl (meth)acrylate, 2-hydroxyethyl (meth)acrylate, 2-hydroxypropyl (meth) acrylate, (meth)acrylic acid, 4-hydroxybutyl (meth)acrylate, 2-hydroxybutyl (meth)acrylate, diethylene glycol mono (meth)acrylate, propylene glycol mono(meth)acrylate, and glycidyl (meth)acrylate; styrenes such as styrene, p-methyl styrene, p-hydroxy styrene, and α-methyl styrene; vinyl ester monomers such as vinyl acetate, vinyl propionate, and vinyl butylate; N-vinyl compounds such as N-vinyl pyrrolidone, N-vinyl formamide, N-vinyl acetamide, and N-vinyl caprolactam; vinyl ethers such as methylvinyl ether, ethylvinyl ether, butylvinyl ether, and hydroxybutylvinyl ether; maleic acid, fumaric acid, itaconic acid, citraconic acid and esters thereof.

The reaction molar ratio between the above-mentioned at least two functional groups-having compound and a compound having both a (meth)acryloyl group and a vinyl ether group may be chosen according to the applications and desired physical properties of the compound having a (meth) acryloyl group. For example, the amount of a compound having both a (meth)acryloyl group and a vinyl ether group is preferably 0.02 to 50 moles with respect to one mole of a functional group in a compound having at least two functional groups, more preferably 0.04 to 10 moles, and furthermore preferably 0.1 to 2 moles.

As for reaction methods in the above-mentioned production method, the addition method, when reacting a compound having at least two functional groups and a compound having both a (meth)acryloyl group and a vinyl ether group, may involve (1) a method feeding these compounds simultaneously at the initial stage of reaction, or (2) a method adding one or both of them continuously or intermittently to the reaction system. In addition, the above-mentioned reaction is preferably carried out in the presence of a catalyst. Catalysts usable in the present invention are suitably acids. Suited for use as the acid are aliphatic monocarboxylic acids such as formic acid, acetic acid, propionic acid, butanoic acid, trichloroacetic acid, dichloroacetic acid, pyruvic acid, and glycolic acid; aliphatic polycarboxylic acids such as oxalic acid, maleic acid, oxalacetic acid, malonic acid, fumaric acid, tartaric acid, and citric acid; aromatic carboxylic acids such as benzoic acid and terephthalic acid; aromatic sulfonic acids and salts thereof such as benzenesulfonic acid, p-toluenesulfonic acid, pyridinium p-toluenesulfonate, and quinolinium p-toluenesulfonate; sulfates such as sodium sulfate, potassium sulfate, magnesium sulfate, calcium sulfate, nickel sulfate, copper sulfate and zirconium sulfate; hydrogensulfates such as sodium hydrogensulfate and potassium hydrogensulfate; mineral acids such as sulfuric acid, hydrochloric acid, hydrobromic acid, hydroiodic acid, phosphoric acid and polyphosphoric acid; heteropoly acids such as phosphomolybdic acid, phosphotungstomolybdic acid and silicotungstomolybdic acid; acidic zeolite; andacidic ionexchange resins, wherein the main structure is a phenol resin or a styrene resin, having any one form of a gel type, a porous type and a macroporous type, and having at least one ion exchange group selected from the group consisting of a sulfonic group and an alkylsulfonic group. These can be used singly or in combination of two or more species. Among them, oxalic acid, maleic acid, potassium hydrogensulfate and hydrochloric acid are preferable. Other acid catalysts, in addition to acting as a catalyst for addition reactions, sometimes act as cationic polymerization initiators for vinyl ether, and therefore it is required to control the temperature strictly. However, hydrochloric acid does not act as a cationic polymerization initiator, but selectively affects addition reactions, and thus allowance for the temperature control is large; as a result, it is very advantageous in production.

The amount of the above-mentioned catalyst to be used may appropriately be adjusted according to the species, the combination, etc. of a compound having at least two functional groups and a compound having both a (meth)acryloyl group and a vinyl ether group to be used for reactions. However, in terms of the yield, the stability of catalyst, productivity and cost efficiency, the amount is, for example, preferably 0.0005 to 1 part by mass relative to 100 parts by mass of the compound having both a (meth)acryloyl group and a vinyl ether group, more preferably 0.001 to 0.5 part by mass. When a halogen acid is used as the catalyst, it is preferable to deactivate the catalyst after the reaction by neutralizing the catalyst with alkali, such as sodium hydroxide, or by adding an epoxy group containing-compound, such as glycidyl (meth)acrylate, and epoxy resins and making the catalyst to add to the epoxy groups.

Further, in the production method of the present invention, a compound having both a (meth)acryloyl group and a vinyl ether group and a compound having a (meth)acryloyl group, which is a product, are both polymerizable compounds. Therefore, the reaction is preferably performed in the presence of a polymerization inhibitor, which can suppress the polymerization and improve the yield.

The above-mentioned polymerization inhibitors suitably include quinone-based polymerization inhibitors such as hydroquinone, methoxyhydroquinone, benzoquinone, and p-tert-butylcatechol; alkylphenol-based polymerization inhibitors such as 2,6-di-tert-butylphenol, 2,4-di-tert-butylphenol, 2-tert-butyl-4,6-dimethylphenol, 2,6-di-tert-butyl-4-methylphenol, and 2,4,6-tri-tert-butylphenol; amine-based polymerization inhibitors such as alkylated diphenylamines, N,N'-diphenyl-p-phenylenediamine, and phenothiazine; N-oxyls such as 4-hydroxy-2,2,6,6-tetramethylpiperidine-N-oxyl; and copper dithiocarbamate-based polymerization inhibitors such as copper dimethyldithiocarbamate, copper diethyldithiocarbamate, and copper dibutyldithiocarbamate. These may be used singly or in combination of two or more species. Among these, quinone-based polymerization inhibitors and N-oxyl polymerization inhibitors are preferable, and hydroquinone, methoxyhydroquinone, benzoquinone, p-tert-butylcatechol, phenothiazine, and 4-hydroxy-2,2,6,6-tetramethylpiperidine-N-oxyl are suitably used.

The amount of the above-mentioned polymerization inhibitor to be added may appropriately be adjusted according to the species, etc. of a compound having at least two functional groups and a compound having both a (meth) acryloyl group and a vinyl ether group. However, in terms of the polymerization suppression effect, yield, productivity and cost efficiency, the amount is, for example, preferably 0.001 to 5 parts by mass relative to 100 parts by mass of the (meth)acrylate, more preferably 0.005 to 1 part by mass, and particularly preferably 0.01 to 0.1 part by mass.

In the production method of the present invention, it is not necessary to use a solvent particularly, but one or two or more species of organic solvents can be used. Organic solvents suitably include aromatic hydrocarbons such as benzene, toluene, and xylene; aliphatic hydrocarbons such as pentane, hexane, cyclohexane and heptane; ethers such as diethyl ether, and diisopropyl ether; ketones such as acetone and methylethyl ketone; polar solvents such as dimethyl formamide and dimethyl sulfoxide; halogenated hydrocarbons such as chloroform, methylene chloride, dichloroethane, and chlorobenzene; ethylene glycol dimethyl ether, ethylene glycol diethyl ether, ethylene glycol dipropyl ether, propylene glycol dimethyl ether, propylene glycol diethyl ether, diethylene glycol dimethyl ether, diethylene glycol diethyl ether; ethylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monoethyl ether acetate, diethylene glycol monopropyl ether acetate, diethylene glycol monobutyl ether acetate, diethylene glycol monophenyl ether acetate, propylene glycol monomethyl ether acetate, dipropylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, (di)methyl glutarate, (di)methyl succinate, (di)methyl adipate; acetone, methyl ethyl ketone, diethyl ketone, methyl isobutyl ketone, ethyl isobutyl ketone, tetrahydrofuran, cyclohexanone, methyl propionate, ethyl propionate, propyl propionate, isopropyl propionate, methyl-3-methoxy propionate, ethyl-3-methoxy propionate, ethyl-3-ethoxy propionate, ethyl-3-propoxy propionate, propyl-3-methoxy propionate, isopropyl-3-methoxy propionate, methyl lactate, ethyl lactate, propyl lactate, isopropyl lactate, butyl lactate, amyl lactate, ethyl ethoxyacetate, ethyl oxyacetate, methyl acetate, ethyl acetate, propyl acetate, isopropyl acetate, butyl acetate, isoamyl acetate, methyl carbonate, ethyl carbonate, propyl carbonate, butyl carbonate, methyl pyruvate, ethyl pyruvate, propyl pyruvate, butyl pyruvate, methyl acetoacetate, ethyl acetoacetate, benzyl methyl ether, benzyl ethyl ether, dihexyl ether, benzyl acetate, ethyl benzoate, diethyl oxalate, diethyl maleate, γ-butyrolactone.

The amount of the above-mentioned organic solvents to be used may appropriately be adjusted according to the species, the combination, etc. of a compound having at least two functional groups and a compound having both a (meth)acryloyl group and a vinyl ether group. However, in terms of the yield, productivity and cost efficiency, the amount is preferably 0 to 200 parts by mass relative to 100 parts by mass of the total mass of these compounds, more preferably 0 to 100 parts by mass, and particularly preferably 0 to 70 parts by mass.

As for the reaction conditions in the production method of the present invention, for example, the reaction temperature is preferably −40 to 150° C. in terms of the yield, productivity, and cost efficiency. The reaction temperature is more preferably −30 to 100° C., and particularly preferably −20 to 70° C. The reaction time may appropriately be adjusted to complete the above-mentioned reaction according to the species, the combinations, the amount of use, etc. of a compound having at least two functional groups, a compound having both a (meth)acryloyl group and a vinyl ether group, a catalyst and a solvent to be used. The reaction pressure may appropriately be adjusted according to the species of a compound having at least two functional groups and a compound having both a (meth)acryloyl group and a vinyl ether group, and to the reaction temperature, etc., and may be at any of normal pressure (atmospheric pressure), reduced pressure and increased pressure if the reaction system can be kept in a liquid state.

The present invention is also concerned with a compound having a (meth)acryloyl group which is obtained by an addition reaction of a functional group of a compound (A) having at least two functional groups and the vinyl ether group of a compound (B) having both a (meth)acryloyl group and a vinyl ether group, the functional groups of the compound (A) being selected from the group consisting of a hydroxyl group, a carboxyl group and a thiol group.

According to the present invention, a compound (A) having at least two functional groups, which is selected from the group consisting of a hydroxyl group, a carboxyl group and a thiol group, and compound (B) having both a (meth)acryloyl group and a vinyl ether group each may be used singly or in combination of two or more species. When two or more species of any one or both of these compounds are used, a compound having a (meth)acryloyl group to be produced becomes two or more species. The compound of the present invention may also be in a form of a low molecular weight compound or an oligomer or a polymer.

The above-mentioned compound (A) having at least two functional groups, being selected from the group consisting of a hydroxyl group, a carboxyl group and a thiol group, is preferably the one being selected from the group consisting of an epoxy acrylate, an unsaturated polyester, a phenol resin, an epoxy resin, a phenoxy resin and a hydroxyl group-containing polymer. As such a compound, compounds mentioned above are suitable.

As for the process for producing a compound having a (meth)acryloyl group of the present invention, the above-mentioned production method are suitably applied. Thus, to produce a compound having a (meth)acryloyl group of the present invention with such production method is a preferable embodiment of the present invention. Specifically, the following production method is preferable; a production method which comprises reacting a compound having at least two functional groups, which is selected from the group consisting of a hydroxyl group, a carboxyl group and a thiol group, with a (meth)acrylate represented by the above general formula (3).

The present invention further provides a compound having a (meth)acryloyl group which has in a molecule at least two of (meth)acryloyl group-containing groups, the (meth)acryloyl group-containing groups being a group represented by the general formula (1):

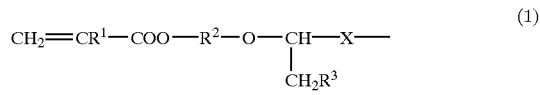

wherein $R^1$ represents a hydrogen atom or a methyl group, $R^2$ represents an organic moiety, $R^3$ represents a hydrogen atom or an organic moiety, and X represents an oxygen or a sulfur atom, and/or a group represented by the general formula (2):

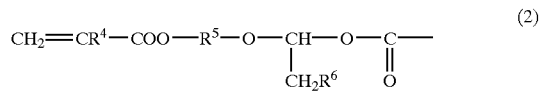

wherein $R^4$ represents a hydrogen atom or a methyl group, $R^5$ represents an organic moiety, $R^6$ represents a hydrogen atom or an organic moiety.

In a compound having a (meth)acryloyl group of the present invention, the number of functional groups represented by the general formula (1) and/or the general formula (2) in a molecule of the compound having a (meth)acryloyl group, if it is two or more, is not particularly restricted. However, when the number of (meth)acryloyl groups in a molecule of the compound is more than two, a cured material, which is further excellent in curing properties and has higher Tg, can be obtained. A compound of the present invention may also be in a form of a low molecular weight compound or an oligomer or a polymer.

Further, a molecular structure connecting with the groups represented by the above general formula (1) and/or (2) may appropriately be selected according to the use and the like of the compound and is not particularly restricted. Suitable structure is the one comprising the structure of an epoxy acrylate, an unsaturated polyester, a phenol resin, an epoxy resin, a phenoxy resin or a hydroxyl group-containing polymer.

As for the production method of a compound having a (meth)acryloyl group of the present invention, for example, the above-mentioned production methods are suitably applied. To produce a compound having a (meth)acryloyl group with such production method is a preferable embodiment of the present invention. In the concrete, a method is preferable that comprises reacting a compound containing a hydroxyl group with a (meth)acrylate represented by the above general formula (3).

A compound having a (meth)acryloyl group of the present invention is obtainable by reacting a compound (A) having at least at least two functional groups, which is selected from the group consisting of a hydroxyl group, a carboxyl group and a thiol group, with a compound (B) having both a (meth)acryloyl group and a vinyl ether group. The compound thus obtained contains a (meth)acryloyl group indispensably and may further contain a carboxyl group in combination with the (meth)acryloyl groups. By containing a carboxyl group, the compound exhibits photo curing properties and alkali developability sufficient to fine pattern formation, and excellent photolithography properties, when used as a photo resist material.

The processes for obtaining the above-mentioned compound having both a (meth)acryloyl group and a carboxyl group suitably include (1) a method that involves setting the ratio of compound (A) having at least one species of functional group selected from the group consisting of a hydroxyl group, a carboxyl group and a thiol group, to compound (B) having both a (meth)acryloyl group and a vinyl ether group and reacting them in a manner that the hydroxyl group and the thiol group remain, and subsequently incorporating a carboxyl group by addition of an acid anhydride to the remaining hydroxyl group and thiol group by ring opening, when a compound having a (meth)acryloyl group is obtained as described above, and (2) a method that involves setting the ratio of compound (A) and compound (B) and reacting them in a manner that the carboxyl group remains when a compound having a (meth) acryloyl group is obtained; however, it is no doubt that the present invention is by no means restricted to these methods.

The concentration of the carboxyl group in the above-mentioned compound having both a (meth)acryloyl group and a carboxyl group is preferably in the range of 20 to 200 mg KOH/g as the acid value, and more preferably in the range of 30 to 150 mg KOH/g. When the acid value is less than 20 mg KOH/g, the removal of an uncured portion is hardly and not rapidly in an alkaline developing solution after light exposure and it may be difficult to form fine pattern with good reproductively and precisely. When the acid value is more than 200 mg KOH/g, a photo-cured portion is also likely to be eroded in alkali developing, and it may be difficult to form fine pattern with good reproductively and precisely.

Acid anhydrides, which are used to incorporate a carboxyl group into the above-mentioned compound having a (meth) acryloyl group by ring opening addition to a hydroxyl group and a thiol group contained in the compound, suitably include phthalic anhydride, succinic anhydride, octenylsuccinic anhydride, pentadodecenylsuccinic anhydride, maleic anhydride, tetrahydrophthalicanhydride, hexahydrophthalic anhydride, methyltetrahydrophthalic anhydride, 3,6-endmethylene tetrahydrophthalic anhydride, methylendmethylene tetrahydrophthalic anhydride, tetrabromophthalic anhydride, dibasic anhydride such as compounds obtained by reacting 9,10-dihydro-9-oxa-10-phosphaphenanthrene-10-oxide with itaconic anhydride or maleic anhydride; trimellitic anhydride; aliphatic or aromatic tetrabasic dianhydride such as biphenyl tetracarboxylic dianhydride, naphthalene tetracarboxylic dianhydride, diphenyl ether tetracarboxylic dianhydride, butane tetracarboxylic dianhydride, cyclopentane tetracarboxylic dianhydride, pyromellitic dianhydride and benzophenone tetracarboxylic dianhydride. These can be used singly or in combination of two or more species.

A compound having a (meth)acryloyl group of the present invention is highly polymerizable and of high crosslinking properties. Further, the compound is capable of making a reduction in permittivity and viscosity since the compound can block or reduced the polar group in the compound. Such a compound having a (meth)acryloyl group may be used singly, or as a composition containing a crosslinker, an additive, a reinforcement, etc. Since such compound, and composition comprising the compound can be cured by heat or light and form a cured material having a high glass transition temperature (Tg) and being excellent in physical properties such as heat resistance, they are suitably applicable to a various applications of matrices for composite material, casting materials, ink, coatings, paints, adhesives, various resist materials relating to electronic parts, printing plates, etc. in the fields of housing, construction and building, electric, electronic and information, transportation and so forth.

In addition, the production method of the present invention can simply and easily produce the above-mentioned compound having a (meth)acryloyl group under mild conditions.

As the above-mentioned crosslinker, a reactive diluent, etc is suitable. Reactive diluents include radical polymerizable monomers that include aromatic vinyl-based monomers such as styrene, $\alpha$-methylstyrene, $\alpha$-chlorostyrene, vinyltoluene, divinylbenzene, diallylphthalate, and diallylbenzenephosphonate; vinyl ester monomers such as vinyl acetate and vinyl adipate; (meth)acrylic monomers such as alkyl (meth)acrylates containing 1 to 18 carbon atoms, alcohol ethylene oxide derivative (meth)acrylates containing 1 to 8 carbon atoms, (alkyl)phenol ethylene oxide derivative (meth)acrylates containing 1 to 18 carbon atoms, diol di(meth)acrylates containing 2 to 9 carbon atoms, polyethylene glycol di(meth)acrylate, polypropylene glycol di(meth)acrylate, bisphenol A ethylene oxide derivative di(meth)acrylate, and glycerin ethylene oxide derivative tri(meth)acrylate; vinyl (thio)ether compounds containing a radical polymerizable double bond such as 2-(vinyloxyethoxy)ethyl (meth)acrylate, 2-(isopropenoxyethoxyethoxy)ethyl (meth)acrylate, 2-(isopropenoxyethoxyethoxyethoxy)ethyl (meth)acrylate, and 2-(isopropenoxyethoxyethoxyethoxyethoxy)ethyl (meth)acrylate; and triallyl cyanurate. These can be used singly or in combination of two or more species according to applications.

In addition, the above-mentioned (meth)acrylic monomers include methyl(meth)acrylate, ethyl(meth)acrylate, butyl(meth)acrylate, $\beta$-hydroxyethyl(meth)acrylate, (2-oxo-1,3-dioxolane-4-il)-methyl (meth)acrylate, (di)ethylene glycol di(meth)acrylate, propylene glycol di(meth)acrylate, trimethylolpropane di(meth)acrylate, trimethylolpropane tri (meth)acrylate, pentaerythritol tetra(meth)acrylate, dipentaerythritol hexa(meth)acrylate, and tri(meth)acrylate of tris(hydroxyethyl)isocyanurate.

The above-mentioned additives and reinforcements suitably include a mold release agent, a lubricant, a plasticizer, an antioxidant, an ultraviolet absorber, a fire retardant, a thickner, a heat (or light) polymerization initiator, a polymerization inhibitor, a diluting solvent, a sensitizer, a coloring agent, an antifoaming agent, a coupling agent, a leveling agent, a surfactant, a wetting agent, a dispersion stabilizer, a thixotropic agent, inorganic fillers such as talc, clay, and barium sulfate; a conductivity donor, a drying inhibitor, a penetrating agent, a pH adjuster, a metal sequesterant, an anti-fungus and mold agent, and other well-known additives. In addition, according to the purpose of applications, following compounds may be added in a range without decreasing above-mentioned characteristics; epoxy resins, unsaturated polyesters, urethane (meth) acrylate, polyester (meth)acrylate, epoxy acrylate, oxazoline compounds, oxetane compounds, or epoxy curing agents such as dicyandiamide or imidazole compounds. Furthermore, a various reinforcing fibers can be utilized as supporting fibers to yield fiber-reinforced composite materials.

When a composition comprising a compound having a (meth)acryloyl group of the present invention is cured by heat or light, a thermal- or photo-polymerization initiator is used.

As the above-mentioned thermal-polymerization initiators, well known compounds can be used that include organic peroxides such as methylethylketone peroxide, benzoyl peroxide, dicumylperoxide, t-butyl hydroperoxide, cumene hydroperoxide, t-butylperoxyoctoate, t-butylperoxybenzoate, and lauroyl peroxide; and azo-based compounds such as azobisisobutyronitrile. In addition, a curing accelerator may be mixed and used during thermal-polymerization. Curing accelerators suitably include cobalt naphthenate, cobalt octylate, etc., and tertiary amines and the like. The amount of thermal-polymerization initiator to be used is preferably 0.05 to 5 parts by mass relative to 100 parts by mass of the above-mentioned composition.

As the above-mentioned photo polymerization initiators, well known compounds can be used that include benzoin and its alkyl ethers thereof such as benzoin, benzoin methyl ether, benzoin ethyl ether, benzoin isopropyl ether, and benzoin isobutyl ether; acetophenones such as acetophenone, 2,2-dimethoxy-2-phenylacetophenone, 1,1-dichloroacetophenone, 4-(1-t-butyldioxy-1-methylethyl) acetophenone, 2-methyl-1-[4-(methylthio)phenyl]-2-morpholino-propane-1-on or 2-benzyl-2-dimethylamino-1-(4-morpholinophenyl)-butanone-1, diethoxyacetophenone, 2-hydroxy-2-methyl-1-phenylpropane-1-on, benzyldimethylketal, 4-(2-hydroxyethoxy)phenyl-(2-hydroxy-2-propyl)ketone, 1-hydroxycyclohexylphenylketone, and 2-hydroxy-2-methyl-1-[4-(1-methylvinyl)phenyl]propanone oligomer; anthraquinones such as 2-methylanthraquinone, 2-amylanthraquinone, 2-t-butylanthraquinone, and 1-chloroanthraquinone; thioxanthones such as 2,4-dimethylthioxanthone, 2,4-diisopropylthioxanthone, 2-chlorothioxanthone, 2-isopropylthioxanthone, 4-isopropylthioxanthone, 2,4-diethylthioxanthone, 2,4-dichlorothioxanthone, 1-chloro-4-propoxythioxanthone, and 2-(3-dimethylamino-2-hydroxy)-3,4-dimethyl-9H-thioxanth one-9-on mesochloride; ketals such as acetophenone dimethylketal and benzyl dimethylketal; benzophenones such as benzophenone, 4-(1-t-butyldioxy-1-methylethyl)benzophenone, 3,3',4,4'-tetrakis(t-butyldioxycarbonyl)benzophenone, methyl o-benzoylbenzoate, 4-phenyl benzophenone, 4-benzoyl-4'-methyl-diphenylsulfide, 3,3',4,4'-tetra(t-butylperoxylcarbonyl)benzophenone, 2,4,6-trimethylbenzophenone, 4-benzoyl-N,N-dimethyl-N-[2-(1-oxo-2-propenyloxy)ethyl]benzenmethanammonium bromide, and (4-benzoylbenzyl)trimethylammonium chloride; acylphosphine oxides and xanthones. A photo polymerization initiator is used in a species or in a mixture of two species or more, and the amount of use is preferably 0.1 to 25 parts by mass relative to 100 parts by mass of the above-mentioned composition.

When a composition comprising a compound having a (meth)acryloyl group of the present invention is, for example, applied to a substrate and irradiated with light to obtain a cured film, the above organic solvents may be mixed in the composition, in terms of applicability, printing properties, workability, etc. These may be used singly or two more of them may be used in combination.

The amount of the above-mentioned solvent can be appropriately used so that the viscosity is optimal during application operation, and is preferably not more than 1000 parts by mass relative to 100 parts by mass of the composition, and more preferably not more than 500 parts by mass.

When a composition comprising a compound having a (meth)acryloyl group of the present invention is used for photolithography, if the composition comprises a compound having a (meth)acryloyl group without having allowed a carboxyl group to be introduced thereto, it is applied to a substrate and exposed to light to obtain a cured film, and then the light un-exposed portion can be solvent developed using the above-mentioned solvent or a halogen-based solvent such as trichloroethylene.

In addition, when a composition comprises a compound having a (meth)acryloyl group with a carboxyl group introduced thereto, alkali development can be performed because the light un-exposed portion is soluble in an alkaline solution.

Developing solutions used for the above-mentioned alkali development suitably include metal alkaline solutions such as sodium hydroxide, potassium hydroxide, potassium carbonate, sodium carbonate, sodium silicate, calcium hydroxide, etc.; an aqueous ammonium solution; and aqueous solutions of water-soluble amines such as monomethyl amine, dimethyl amine, trimethyl amine, monoethyl amine, diethyl amine, triethyl amine, monopropyl amine, dimethylpropyl amine, monoethanol amine, diethanol amine, triethanol amine, ethylenediamine, diethylene triamine, dimethylaminoethyl methacrylate, and polyethylene imine. Of these, a species or a mixture of two species or more can be used. In particular, a dilute aqueous alkaline solution of 1.5% by mass or less is suitably used.

A composition comprising a compound having a (meth) acryloyl group of the present invention is suited to being (1) a photo-curable composition, or (2) an aqueous photo-curable composition. A photo-curable composition of the above (1) comprises a compound having a (meth)acryloyl group of the present invention and a photo polymerization initiator, then in this photo-curable composition, the above can be used for a photo polymerization initiator. The amount of photo polymerization initiator to be used is preferably not less than 0.1% by mass relative to 100% by mass of the photo-curable composition, and not more than preferably 25% by mass. When the amount is less than 0.1% by mass, failure in photo exposure curing may occur. Exceeding 25% by mass may lead to deteriorations of film coating properties, abrasion resistance and chemical resistance of a cured film after light exposure, etc. More preferably not less than 0.5% by mass, but not more than 15% by mass.

In addition, a photo-curable composition of the above-mentioned (1) may be formulated a radical polymerizable compound that can participate in photo polymerization reaction.

The above-mentioned radical polymerizable compounds include, in addition to the above-mentioned radical polymerizable monomers, radical polymerizable oligomers in which unsaturated polyesters, urethane acrylates, epoxyacrylate, polyester acrylates, etc. can be used. These radical polymerizable compounds can be used singly or in a mixture of two species or more, and are preferably mixed in an amount of 5 to 500 parts by mass relative to 100 parts by mass of a compound having a (meth)acryloyl group according to applications and required physical properties.

Addition of a thermosetting component such as an oxazoline compound, an oxetane compound or an epoxy resin or a curing agent such as dicyandiamide or an imidazole compound to a photo-curable composition of the above-mentioned (1) can improve the heat resistance, solvent resistance and water resistance of the obtained cured film due to post curing of the film after image formation. In particular, when a composition comprising a compound having a (meth)acryloyl group with a carboxyl group introduced thereto is used, the carboxyl group of a hydrophilic group is allowed to react with the above-mentioned thermosetting component in the post curing step to be consumed, which is more effective. In this case, an oxazoline compound is preferably used because of the hydroxyl group being not generated. The above-mentioned thermosetting component is preferably formulated in an amount of 5 to 500 parts by mass relative to 100 parts by mass of a compound having a (meth)acryloyl group. The above-mentioned curing agent is preferably formulated in an amount of 1 to 20 parts by mass relative to 100 parts by mass of the above-mentioned thermosetting component and in an amount of 0.05 to 100 parts by mass relative to 100 parts by mass of a compound having a (meth)acryloyl group.

A method of using a photo-curable composition of the above-mentioned (1) includes directly applying the composition to a substrate in a liquid state, and also applying it to a film such as a polyethylene terephthalate in advance to form a dried dry film (a protection film may be attached) for utilization. In this case, a dry film is laminated on a substrate and the film may be peeled prior to, or subsequent to light exposure.

In addition, a method of imaging by directly scan exposing laser light on a film by means of digitalized data without using a film for pattern forming during light exposure (CTP, computer to plate), as is used in a print plate making, can be adopted. Thus, the above-mentioned photo-curable composition of (1) is preferably used as a photo-curable resin composition for image-forming and such a photo-curable resin composition for image-forming is also one of the preferred embodiments of the present invention.

The above-mentioned photo-curable resin composition for image-forming can be suitably applied to a variety of applications such as a solder resist for printed circuit board production, an etching resist, an electroless plating resist, an insulating layer of a printed circuit board by the buildup method, a black matrix for liquid crystal display production, a color filter, a photo spacer, and a print plate making.

The above-mentioned photo-curable composition made by adding an inorganic powder to a photo-curable composition of (1) is preferably, the inorganic powders suitably include glass fritter such as lead borosilicate glass, zinc borosilicate glass, or bismuth borosilicate glass, which are $PbO—SiO_2$-based, $PbO—B_2O_3—SiO_2$-based, $ZnO—SiO_2$-based, $ZnO—B_2O_3—SiO_2$-based, $BiO—SiO_2$-based, $BiO—B_2O_3—SiO_2$-based; oxides such as cobalt oxides, iron oxide, chromium oxide, nickel oxide, copper oxide, manganese oxide, neodymium oxide, vanadium oxide, cerium oxide, Tipaque yellow, cadmium oxide, alumina, silica, magnesia, spinel, and oxides of Na, K, Mg, Ca, Ba, Ti, Zr, Al, etc.; and fluorescent powders such as ZnO: Zn, $Zn_3(PO_4)_2$: Mn, $Y_2SiO_5$: Ce, $CaWO_4$: Pb, $BaMgAl_{14}O_{23}$: Eu, ZnS: (Ag, Cd), $Y_2O_3$: Eu, $Y_2SiO_5$: Eu, $Y_3Al_5O_{12}$: Eu, $YBO_3$: Eu, (Y, Gd)$BO_3$: Eu, $GdBO_3$: Eu, $ScBO_3$: Eu, $LuBO_3$: Eu, $Zn_2SiO_4$: Mn, $BaAl_{12}O_{19}$: Mn, $SrAl_{13}O_{19}$: Mn, $CaAl_{12}O_{19}$: Mn, $YBO_3$: Tb, $BaMgAl_{14}O_{23}$: Mn, $LuBO_3$: Tb, $GdBO_3$: Tb, $ScBO_3$: Tb, $Sr_6Si_3O_3Cl_4$: Eu, ZnS: (Cu, Al), ZnS: Ag, $Y_2O_2S$: Eu, ZnS: Zn, (Y, Cd)$BO_3$: Eu, $BaMgAl_{12}O_{23}$: Eu, etc. These may be used singly or two more of them may be used in combination. In addition, when an inorganic powder-containing photo-curable composition of the present invention is used for conductive pattern forming, etc., addition of conductive particles of iron, nickel, copper, aluminum, silver, gold, etc. can attain the objective.

The amount of the above-mentioned inorganic powder to be used is preferably not less than 30% by mass relative to 100% by mass of the photo-curable composition containing an inorganic powder, and not more preferably 95% by mass. When the amount is less than 30% by mass, the problems of deteriorating of film coating properties, printing properties and shrinkage after baking, etc. maybe occurred. When the amount exceeds 95% by mass, there may be the decreasing possibility in photo-curing properties.

The methods of using a photo-curable composition containing the above-mentioned inorganic powder preferably include, for example, (1) a method that involves applying the composition to the whole or partial face of a substrate or forming a pattern by means of imaging, etc., or forming a specified shape, and subsequently curing by irradiation with light such as ultraviolet rays, and (2) a method that involves obtaining a cured pattern or shape by photolithography, and then baking. By curing and baking a photo-curable composition containing an inorganic powder, the organic components in cured materials which comprises a compound having a (meth)acryloyl group decompose and volatilize, in addition the inorganic powders alloyes in fusion each other. Therefore, moldings such as a strong film, and pattern which constituted from inorganic components such as an inorganic powder, etc.

The above-mentioned photo-curable composition and the inorganic powder-containing photo-curable composition are suitably applicable, by imaging or photolithography, etc., to the production of a partition wall, an electrode, a resister, a fluorescent material, a color filter, a black matrix, etc., which are of a plasma display panel (PDP), the production of an electrode pattern constituting a LCD, an organic EL element, a print circuit board, a multi-layer printed circuit board, a multi-chip module, and a LSI, etc., and the production of a conductive pattern on a ceramic board.

In an aqueous photo-curable composition of the above (2), the content ratio (weight ratio) of compound having a (meth)acryloyl group to water (compound having a (meth)acryloyl group/water) is preferably 1/99 or more and preferably 99/1 or less. When the content of the compound having a (meth)acryloyl group is less than 1, the curability of an aqueous photo-curable composition and physical properties of cured material may not be adequately obtained. When the content exceeds 99, the viscosity increases and thus workability may be reduced. The ratio is more preferably not less than 5/95 and not more than 90/10.

The above-mentioned aqueous photo-curable composition preferably contains a photo polymerization initiator. Of the initiators, acetophenones, benzophenones, or acylphosphine oxides are preferable. In particular, a water-soluble photo radical polymerization initiator is preferable.

In the above-mentioned aqueous photo-curable composition, the amount of photo polymerization initiator to be used is preferably not less than 0.1% by mass relative to 100% by mass of a compound having a (meth)acryloyl group and preferably not more than 20% by mass. When the amount is less than 0.1% by mass, sufficient curing properties may not be obtained. When the amount exceeding 20% by mass, it may be disadvantageous from the viewpoint of cost efficiency. The amount is more preferably not less than 0.5% by mass and not more than 15% by mass.

The above-mentioned aqueous composition preferably further contains a coloring agent. Coloring agents suitably include dyes and pigments, which can be used singly or in two species or more. In addition, a dye and a pigment can be used in combination.

The above-mentioned dyes suitably include the following: direct dyes such as C.I. Direct Black 17, 19, 32, 51, 62, 71, 108, 146, 154; C.I. Direct Blue 6, 22, 25, 71, 86, 90, 106, 199; C.I. Direct Red 1, 4, 17, 28, 83; C.I. Direct Yellow 12, 24, 26, 44, 86, 98, 100, 142; C.I. Direct Orange 34, 39, 44, 46, 60; C.I. Direct Violet 47, 48; C.I. Direct Brown 109; C.I. Direct Green 59; acid dyes such as C.I. Acid Black 2, 7, 24, 24, 26, 31, 52, 63, 112, 118; C.I. Acid Blue 9, 22, 40, 59, 93, 102, 104, 113, 117, 120, 167, 229, 234, 254; C.I. Acid Red 1, 6, 8, 32, 37, 51, 52, 80, 85, 87, 92, 94, 115, 180, 256, 317, 315; C.I. Acid Yellow 11, 17, 23, 25, 29, 42, 49, 61, 71; C.I. Acid Orange 7, 19; C.I. Acid Violet 49; reactive dyes such as C.I. Reactive Yellow 2, 3, 13, 15, 17, 18, 23, 24, 37, 42, 57, 58, 64, 75, 76, 77, 79, 81, 84, 85, 87, 88, 91, 92, 93, 95, 102, 111, 115, 116, 130, 131, 132, 133, 135, 136, 137, 139, 140, 142, 143, 144, 145, 146, 147, 148, 151, 162, 163; C.I. Reactive Orange 5, 7, 11, 12, 13, 15, 16, 35, 45, 46, 56, 62, 70, 72, 74, 82, 84, 87, 91, 92, 93, 95, 97, 99; C.I. Reactive Red 3, 13, 16, 21, 22, 23, 24, 29, 31, 33, 35, 45, 49, 55, 63, 85, 106, 109, 111, 112, 113, 114, 118, 126, 128, 130, 131, 141, 151, 170, 171, 174, 176, 177, 183, 184, 186, 187, 188, 190, 193, 194, 195, 196, 200, 201, 202, 204, 206, 218, 221; C.I. Reactive Violet 1, 4, 5, 6, 22, 24, 33, 36, 38; C.I. Reactive Blue 2, 3, 5, 8, 10, 13, 14, 15, 18, 19, 21, 25, 27, 28, 38, 39, 40, 41, 49, 52, 63, 71, 72, 74, 75, 77, 78, 79, 89, 100, 101, 104, 105, 119, 122, 147, 158, 160, 162, 166, 169, 170, 171, 172, 173, 174, 176, 179, 184, 190, 191, 194, 195, 198, 204, 211, 216, 217; C.I. Reactive Green 5, 8, 12, 15, 19, 23; C.I. Reactive Brown 2, 7, 8, 9, 11, 16, 17, 18, 21, 24, 26, 31, 32, 33; C.I. Reactive Black 1, 5, 8, 13, 14, 23, 31, 34, 39; other dyes including C.I Basic Black 2; C.I. Basic Blue 1, 3, 5, 7, 9, 24, 25, 26, 28, 29; C.I. Basic Red 1, 2, 9, 12, 13, 14, 37; C.I. Basic Violet 7, 14, 27; C.I. Food Black 1, 2; and oil soluble dyes such as C.I. Solvent Black 6, C.I. Solvent Black 18, 24, 28, 29, 33, 36, 37, 38, 51; C.I. Solvent Yellow 1, 49, 62, 74, 79, 82, 83, 89, 90, 120, 121, 151, 153, 154; C.I. Solvent Red 25, 31, 86, 92, 97, 118, 132, 160, 186, 187, 219; C.I. Solvent Blue 33, 38, 42, 45, 53, 65, 67, 70, 104, 114, 115, 135.

The above-mentioned pigments suitably include achromatic color pigments such as Carbon Black, titanium oxide and calcium carbonate, and chromatic color organic pigments. Organic pigments suitably include insoluble azo pigments such as Toluidine Red, Toluidine Maroon, Hansa Yellow, Benzidine Yellow, and Pyrazolone Red; soluble azo pigments such as Lithol Red, HelioBordeaux, Pigment Scarlet, and Permanent Red 2B; derivatives from vat dyes such as Alizarin, Indanthrone, and Thioindigo Maroon; phthalocyanine-based organic pigments such as Phthalocyanine Blue and Phthalocyanine Green; quinacridone-based organic pigments such as Quinacridone Red and Quinacridone Magenta; perylene-based organic pigments such as Perylene Red and Perylene Scarlet; isoindolinone-based organic pigments such as Isoindolinone Yellow and Isoindolinone Orange; pyranthrone-based organic pigments such as Pyranthrone Red and Pyranthrone Orange; thioindigo-based organic pigments; condensed azo-based organic pigments; benzimidazolone-based organic pigments; quinophthalone-based organic pigments such as Quinophthalone Yellow; isoindolinone-based organic pigments such as Isoindolinone Yellow; and other pigments including Flavanthrone Yellow, Acylamide Yellow, Nickel Azo Yellow, Copper Azo Methine Yellow, Perinone Orange, Anthrone Orange, Dianthraquinonyl Red, and Dioxazine Violet, etc.

In particular, Carbon Black used as black ink includes Mitsubishi Chemical's No. 2300, No. 900, MCF88, No. 33, No. 40, No.45, No.52, MA7, MA8, MA100, No.2200B available from, Colombia's Raven 5750, Raven5250, Raven5000, Raven3500, Raven1255, Raven700 available from, Cabot's Regal 400R, Regal 330R, Regal 660R, Mogul L, Monarch700, Monarch 800, Monarch 880, Monarch 900, Monarch 1000, Monarch 1100, Monarch 1300, Monarch 1400 available from, and Degussa's Color Black FW1, Color Black FW2, Color Black FW2V, Color Black FW18, Color Black FW200, Color Black S150, Color Black S160, Color Black S170, Printex 35, Printex U, Printex V, Printex 140U, Special Black 6, Special Black 5, Special Black4A, Special Black 4 available from.

In the above-mentioned aqueous photo-curable composition, the amount of coloring agent to be used is preferably not less than 0.5% by mass and not more than 30% by mass relative to 100% by mass of an aqueous photo-curable composition. When the amount is less than 0.5% by mass, a sufficient coloring effect may not be obtained. When the amount exceeding 30% by mass, it may be disadvantageous in cost efficiency. The amount is more preferably not less than 1% by mass and not more than 25% by mass.

The above-mentioned aqueous photo-curable composition can be contained further additives such as a dispersion stabilizer for pigments, etc., an antifoaming agent, a mold release agent, a lubricant, a plasticizer, an antioxidant, an ultraviolet absorber, a fire retardant, a filler, a thickner, a heat (or light) polymerization initiator, a sensitizer, a coloring agent, a coupling agent, a leveling agent, a surfactant, a wetting agent, a thixotropic agent, inorganic fillers such as talc, clay, and barium sulfate; a conductivity donor, a drying inhibitor, a penetrating agent, a pH adjuster, a metal sequesterant, an anti-fungus and mold agent, and other well-known additives. The above-mentioned aqueous photo-curable composition is suitably utilized in a wide variety of fields such as various paints, adhesives, resists, inks for printing, and the like. Methods of application of the aqueous photo-curable composition suitably include methods using a brush, a bar coater, a spray coater, a spinner, and a roll coater, etc. In addition, curing methods suitably include a heat curing method, and a method by activated energy rays. Of these, the curing method by irradiation of activated energy rays is more preferable.

The above-mentioned activated energy rays may be energy rays that can react a compound having a (meth) acryloyl group contained in an aqueous photo-curable composition, and cure the material, which suitably include ultraviolet rays and electron rays. Of these, ultraviolet rays are suitable when they are used in fields of paints and the like.

As for the apparatuses that irradiate ultraviolet rays, a high-pressure mercury lamp, a low-pressure mercury lamp, a metal halide lamp, a fluorescent chemical lamp, and a fluorescent blue lamp can be used.

A compound having a (meth)acryloyl group of the present invention having the above constitution is highly polymerizable and suitably applicable to a various uses. In addition, the compound is highly crosslinkable and thus has a high glass transition temperature (Tg), thereby enabling the formation of a cured material excellent in physical properties such as heat resistance. Furthermore, the compound is allowed to have a low permittivity and a low viscosity, and so these properties can be set properly according to various uses. Also, the process for producing the compound of the present invention, comprising the steps described above, can simply and easily manufacture such a compound having a (meth)acryloyl group under mild conditions. Moreover, a photo-curable composition and an aqueous photo-curable composition of the present invention include such a compound having a (meth)acryloyl group, and therefore are useful compositions that are suitably applicable to diverse uses.

BEST MODES FOR CARRYING OUT THE INVENTION

The present invention will be discussed hereinafter in more detail by means of examples; however, the present invention is by no means limited to the examples only. In addition, "part" refers to "part by weight," unless otherwise indicated.

EXAMPLE 1

114.2 g (hydroxyl group=1 mol) of bisphenol A, 0.017 g (0.1 mmol) of p-toluenesulfonic acid, and 300 g of 2-butanone as solvent were put into a liter flask equipped with a stirrer, a thermometer, a condenser and a nitrogen-introducing tube. The material was agitated and then was cooled to 10° C. in an ice bath. Thereafter, 186.2 g (1 mol) of 2-(vinyloxyethoxy)ethyl acrylate (hereinafter referred to as "VEEA") was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 1:
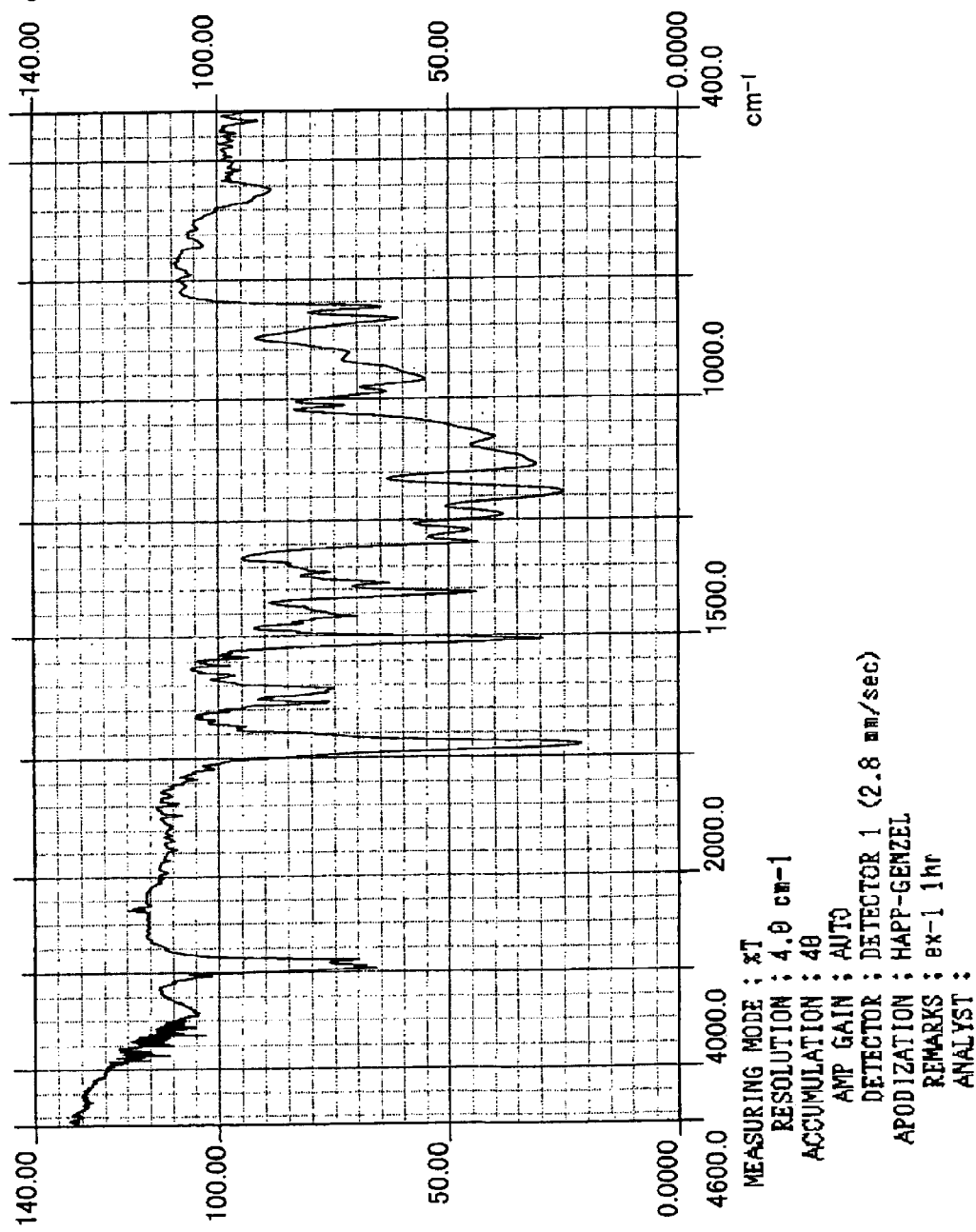
FIG. 1 shows an IR spectrum chart of a reaction product obtained from an Example.
Figure 9:
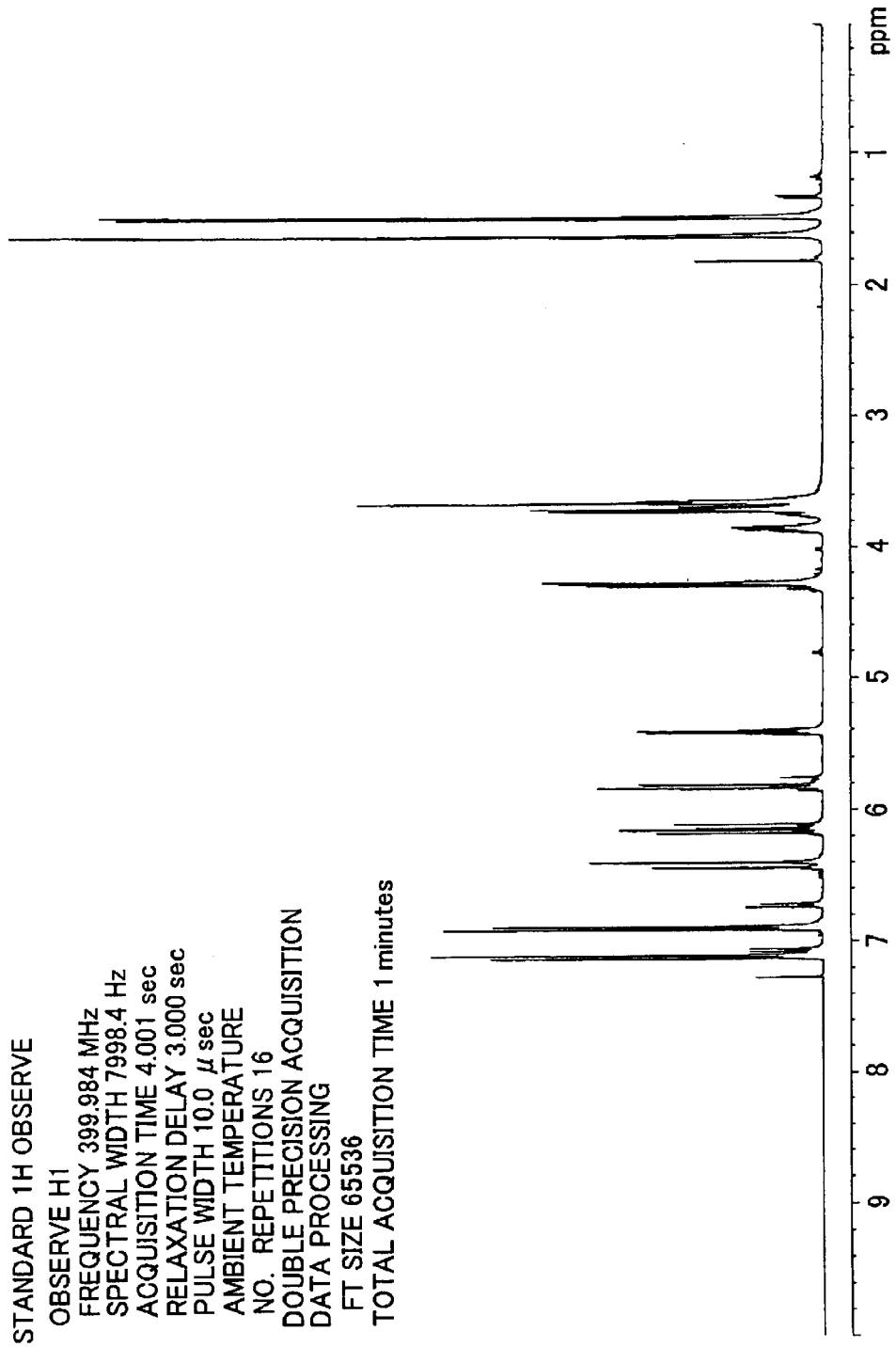
FIG. 9 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 9 shows a chart of $^1$H-NMR of the reaction product and FIG. 1 shows an IR spectrum of the product.

EXAMPLE 2

183.5 g of a bisphenol A epoxy resin (YD-127, product of Tohto Kasei Co. Ltd.) and 0.734 g of triethylbenzyl ammonium chloride were put into a 1 liter flask equipped with a stirrer, a thermometer, a condenser and a nitrogen-introducing tube. Thereafter, the mixture was allowed to react at 115° C. over 5 hours while 72 g of acrylic acid were dropped and added over 2 hours. 0.729 g of hydrochloric acid and 441.7 g of 2-butanone as solvent were added to 255.5 g (hydroxyl group=1 mol) of the obtained epoxy acrylate and stirred, and then the mixture was cooled to 10° C. in an ice bath. Then, 186.2 g (1 mol) of VEEA were dropped and added over 1 hour into the resulting solution, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 2:
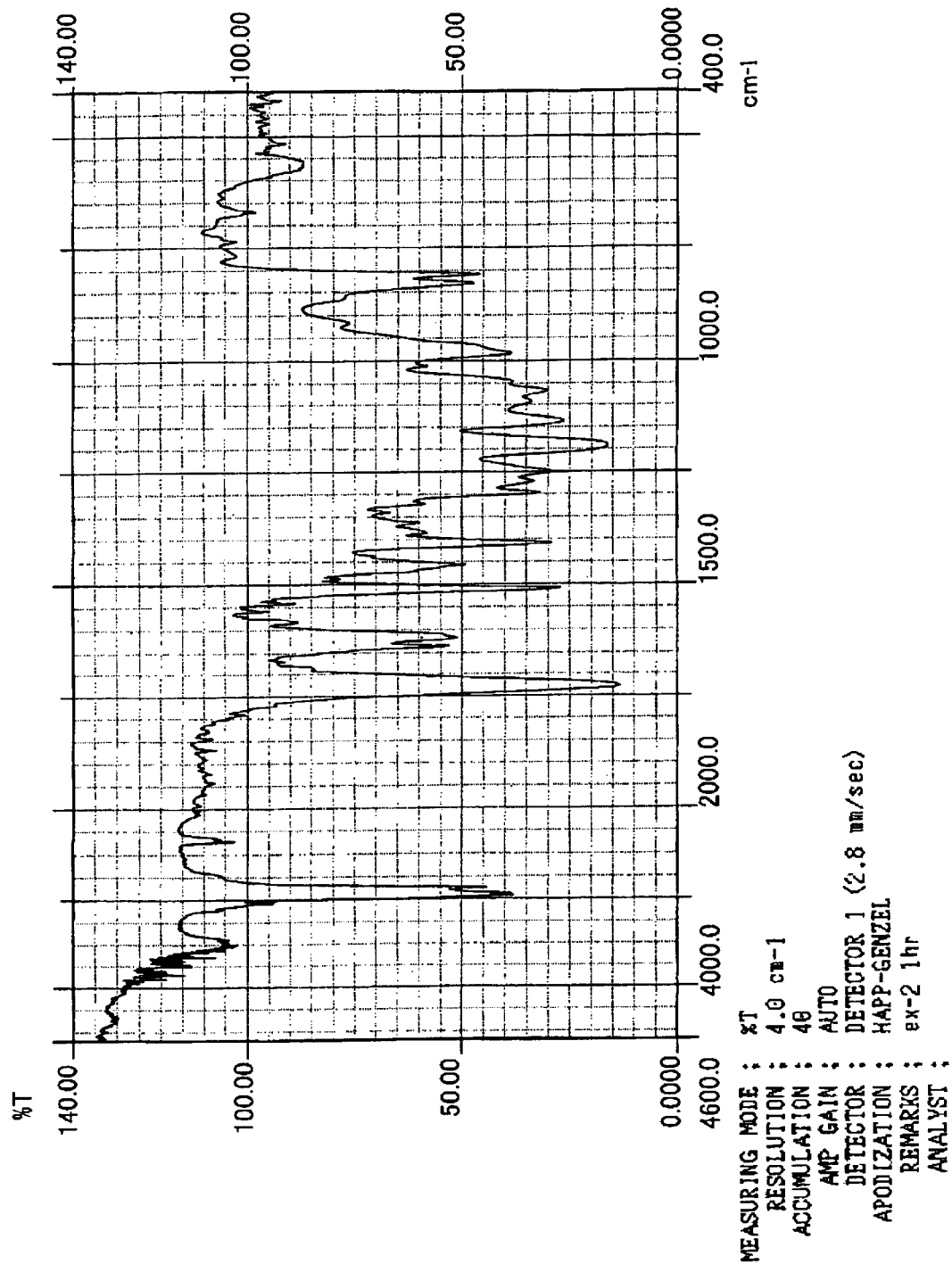
FIG. 2 shows an IR spectrum chart of a reaction product obtained from an Example.
Figure 10:
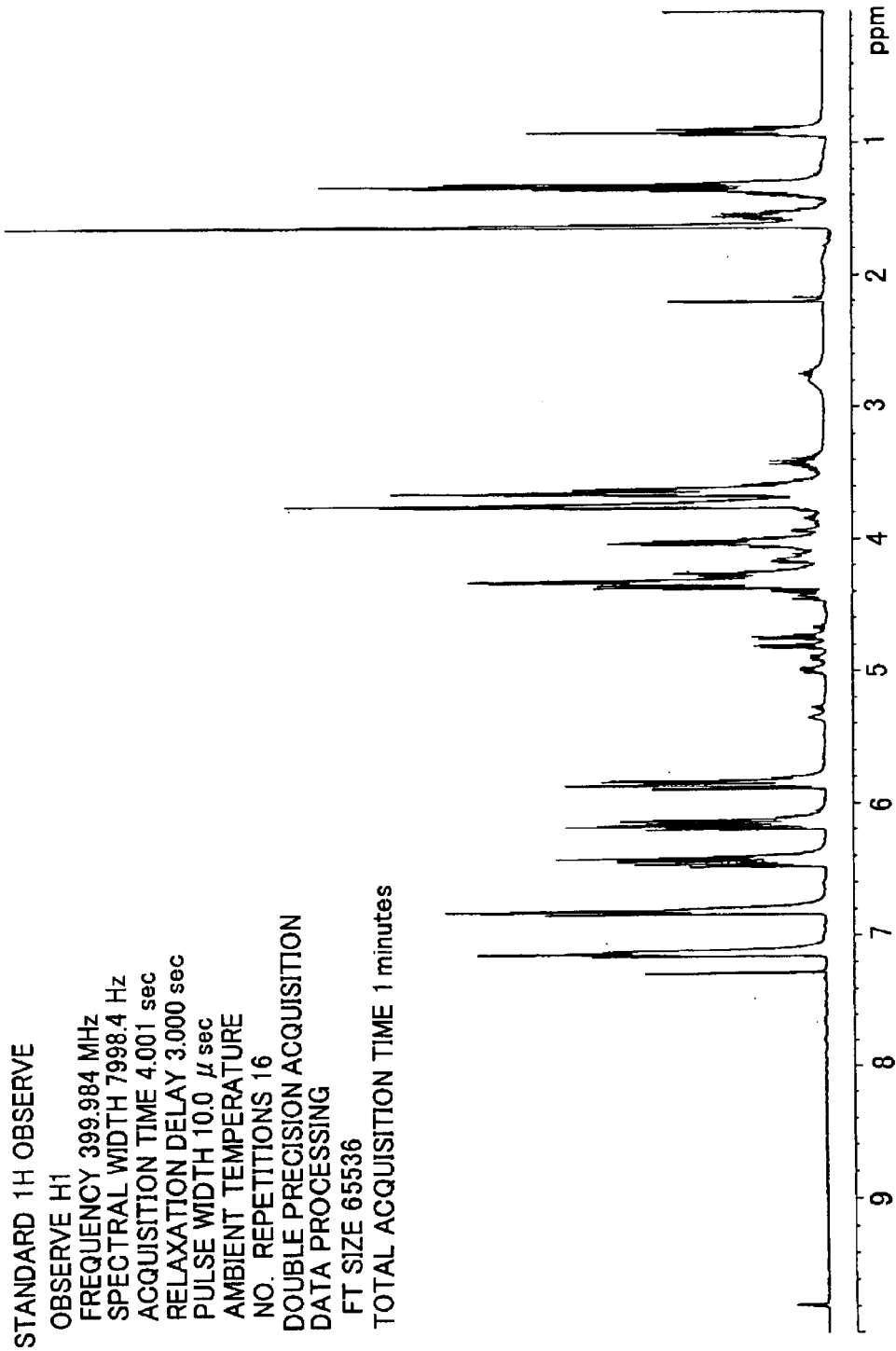
FIG. 10 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 10 shows a chart of $^1$H-NMR of the reaction product and FIG. 2 shows an IR spectrum of the product.

EXAMPLE 3

90 g (0.9 mol) of methyl methacrylate, 13 g (0.1 mol) of 2-hydroxyethyl methacrylate, and 240 g of 2-butanone were put into a 0.5 liter flask equipped with a stirrer, a thermometer, a condenser and a nitrogen-introducing tube. After the air was sufficiently replaced by nitrogen, the temperature was raised to 70° C. Then, 1.03 g of 2,2'-azobis (2,4-dimethylvaleronitrile) dissolved in 2-butanone was introduced into the reaction mixture over 1 hour, and then it was polymerized at 70° C. over 5 hours. To 103 g of the methacrylate polymer thus obtained, 0.073 g of hydrochloric acid was added and the material was cooled to 10° C. in an ice bath. Thereafter, 20.02 g (0.1 mol) of 2-(vinyloxyethoxy) ethyl methacrylate (hereinafter referred to as "VEEM") was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 3:
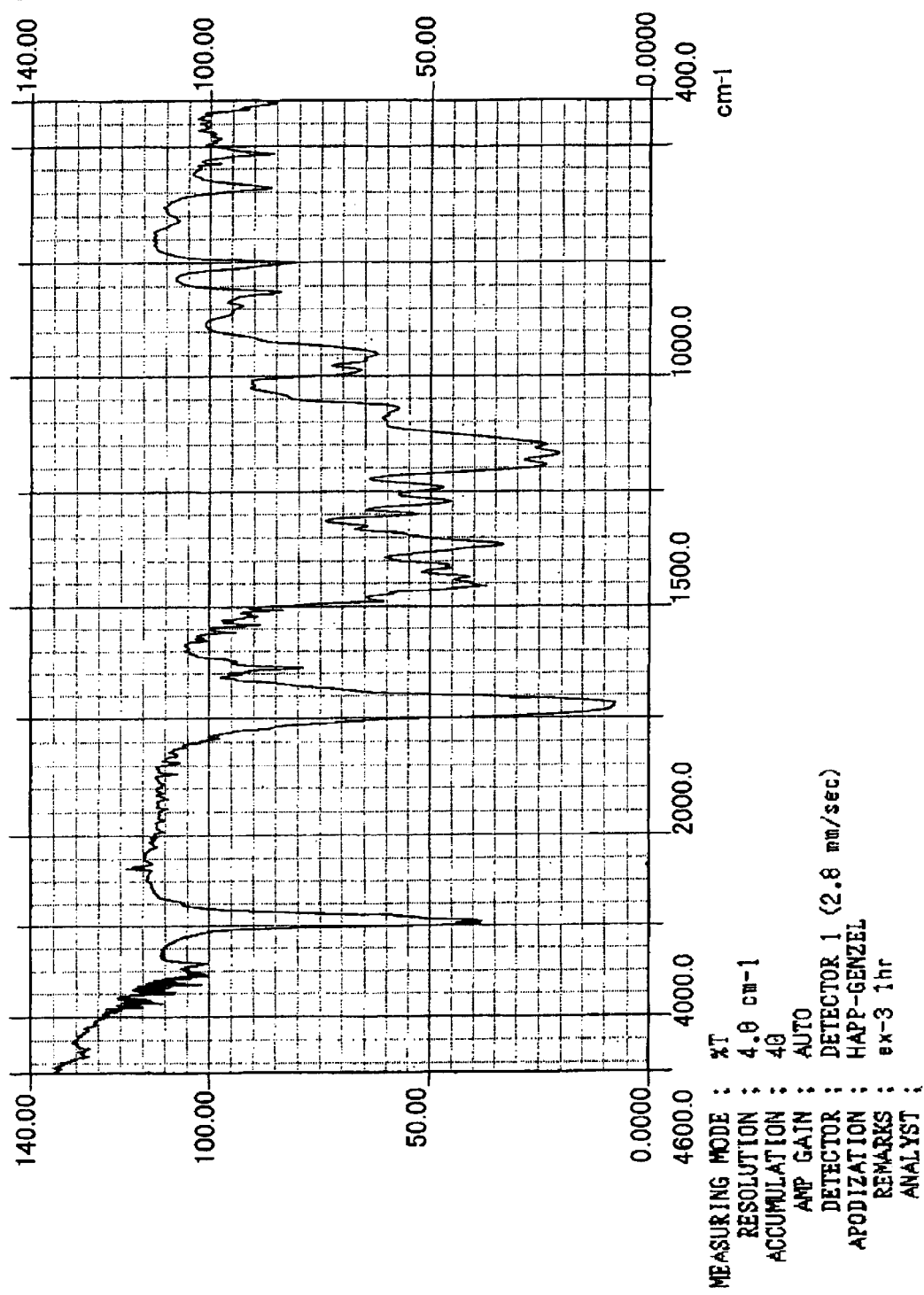
FIG. 3 shows an IR spectrum chart of a reaction product obtained from an Example.
Figure 11:
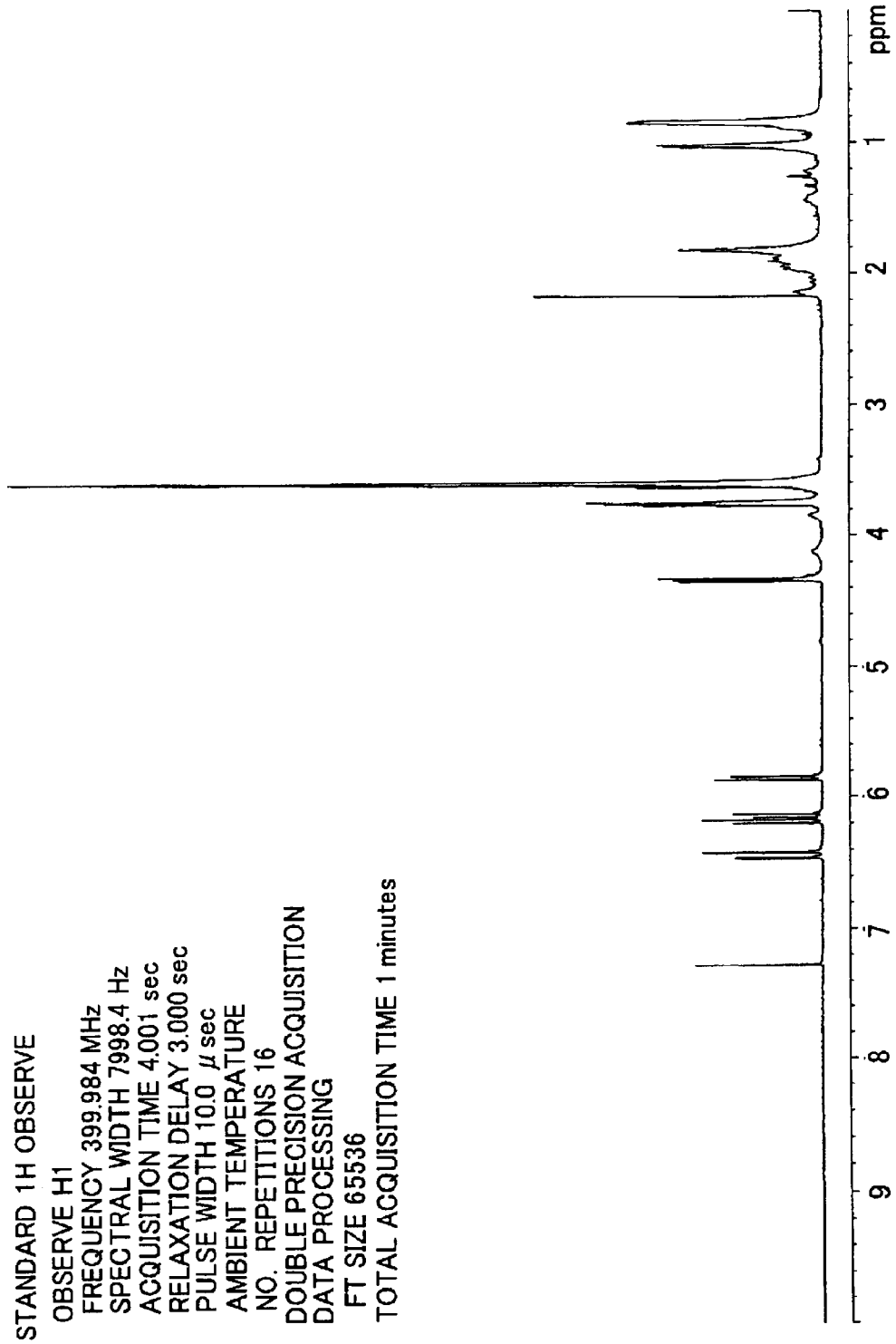
FIG. 11 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 11 shows a chart of $^1$H-NMR of the reaction product and FIG. 3 shows an IR spectrum of the product.

EXAMPLE 4

53.9 g (0.55 mol) of maleic anhydride, 66.7 g (0.45 mol) of phthalic anhydride, 18.6 g (0.30 mol) of ethylene glycol and 57.1 g (0.75 mol) of propylene glycol were put into a 0.5 liter flask equipped with a stirrer, a thermometer, a condenser and a nitrogen-introducing tube. After the air was sufficiently replaced by nitrogen, condensation was carried out at 210° C. over 6 hours to yield an unsaturated polyester with an acid value of 30. 0.078 g of hydrochloric acid and 120 g of 2-butanone were added to 100 g of the obtained unsaturated polyester, and then the mixture was cooled to 10° C. in an ice bath. Then, 19.9 g of VEEA was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 4:
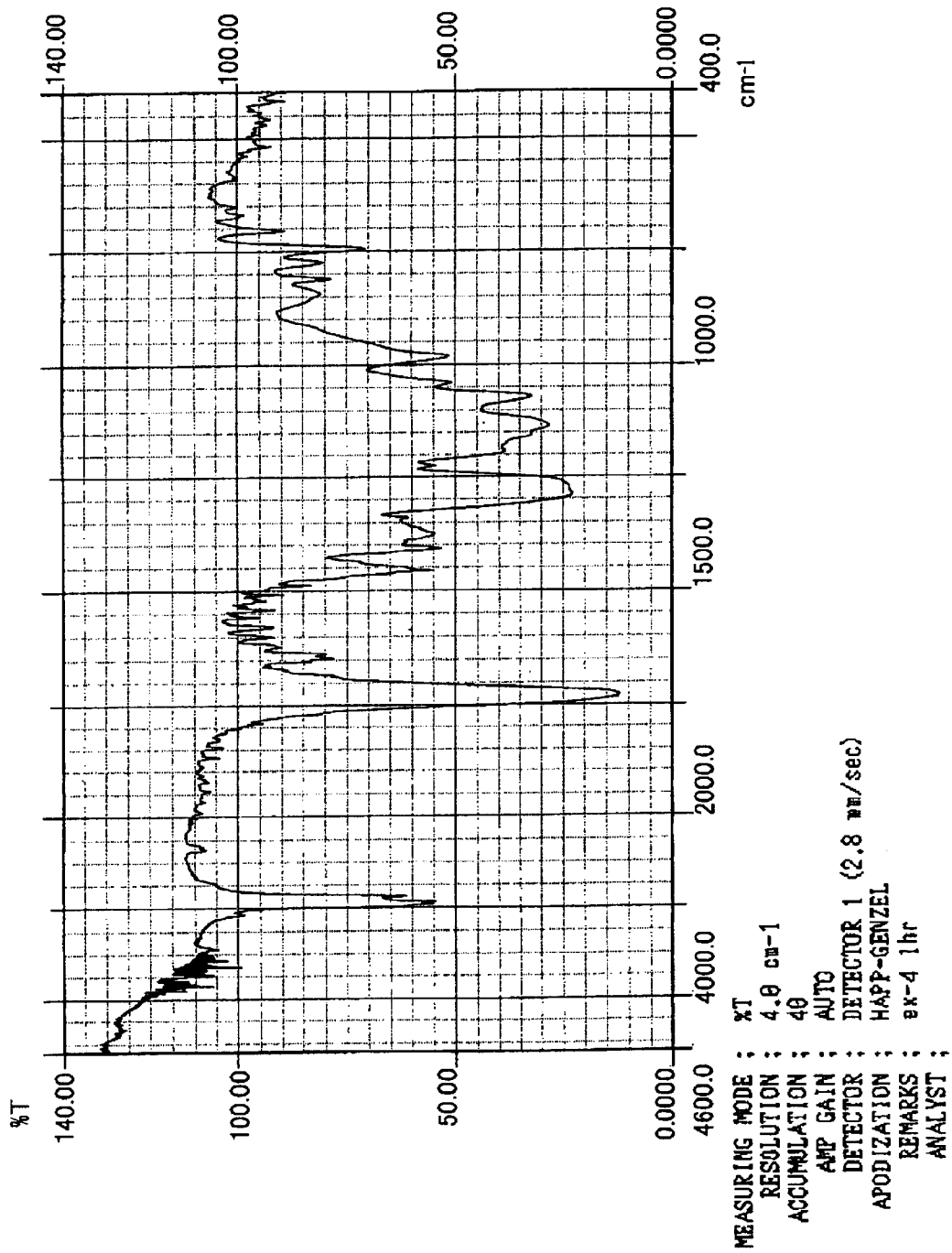
FIG. 4 shows an IR spectrum chart of a reaction product obtained from an Example.
Figure 12:
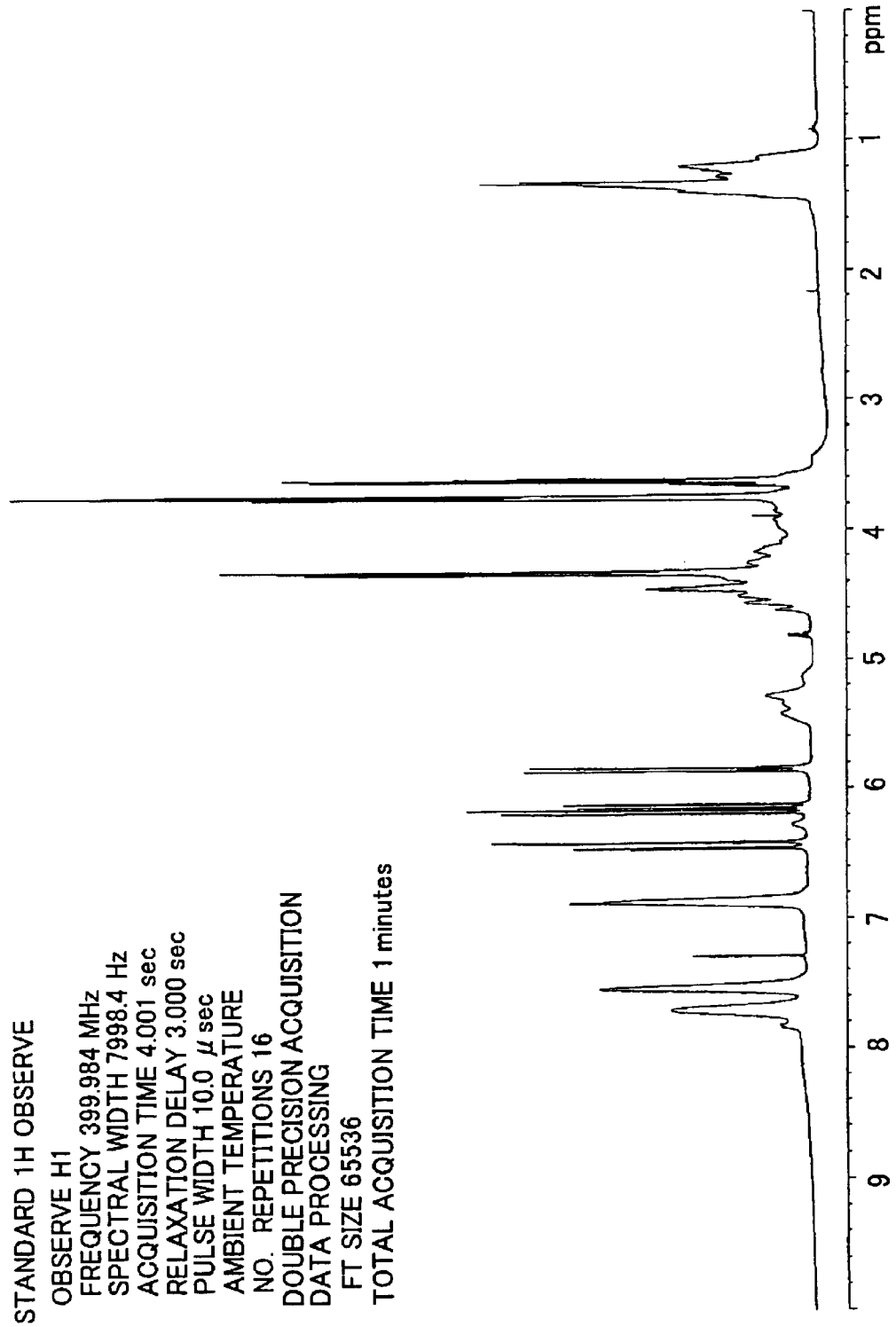
FIG. 12 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 12 shows a chart of $^1$H-NMR of the reaction product and FIG. 4 shows an IR spectrum of the product.

EXAMPLE 5

256.9 g of a bisphenol A epoxy resin (YD-127, product of Tohto Kasei Co. Ltd.), 177.3 g of bisphenol A and 0.217 g of triethylbenzyl ammonium chloride were put into a 1 liter flask equipped with a stirrer, a thermometer, a condenser and a nitrogen-introducing tube, and a reaction was performed at 120° C. over 5 hours. 1.134 g of hydrochloric acid and 310.2 g of 2-butanone as solvent were added to 434.2 g of the obtained phenoxy resin, and stirred, and then the mixture was cooled to 10° C. in an ice bath. Then, 289.6 g of VEEA was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 5:
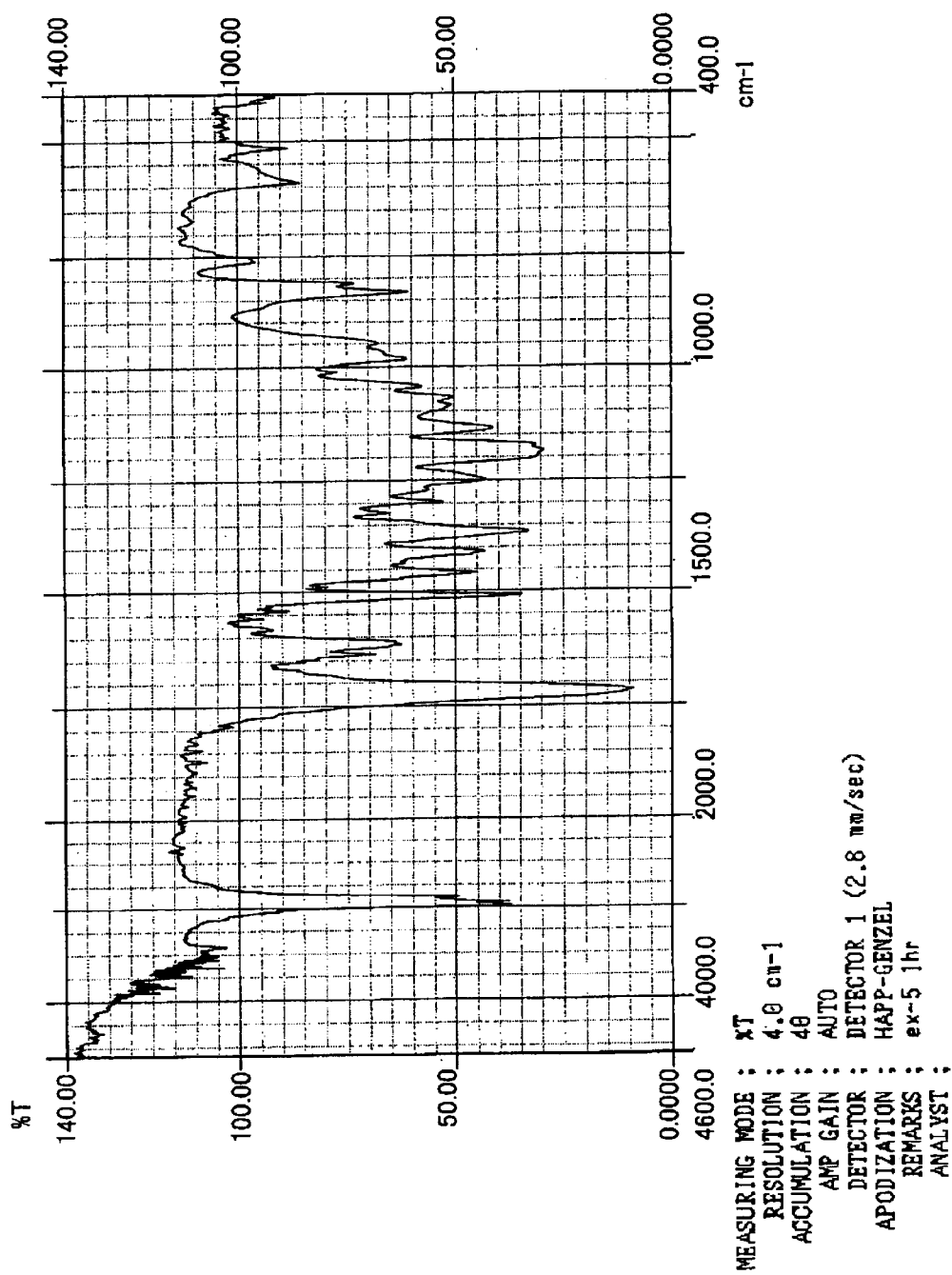
FIG. 5 shows an IR spectrum chart of a reaction product obtained from an Example.
Figure 13:
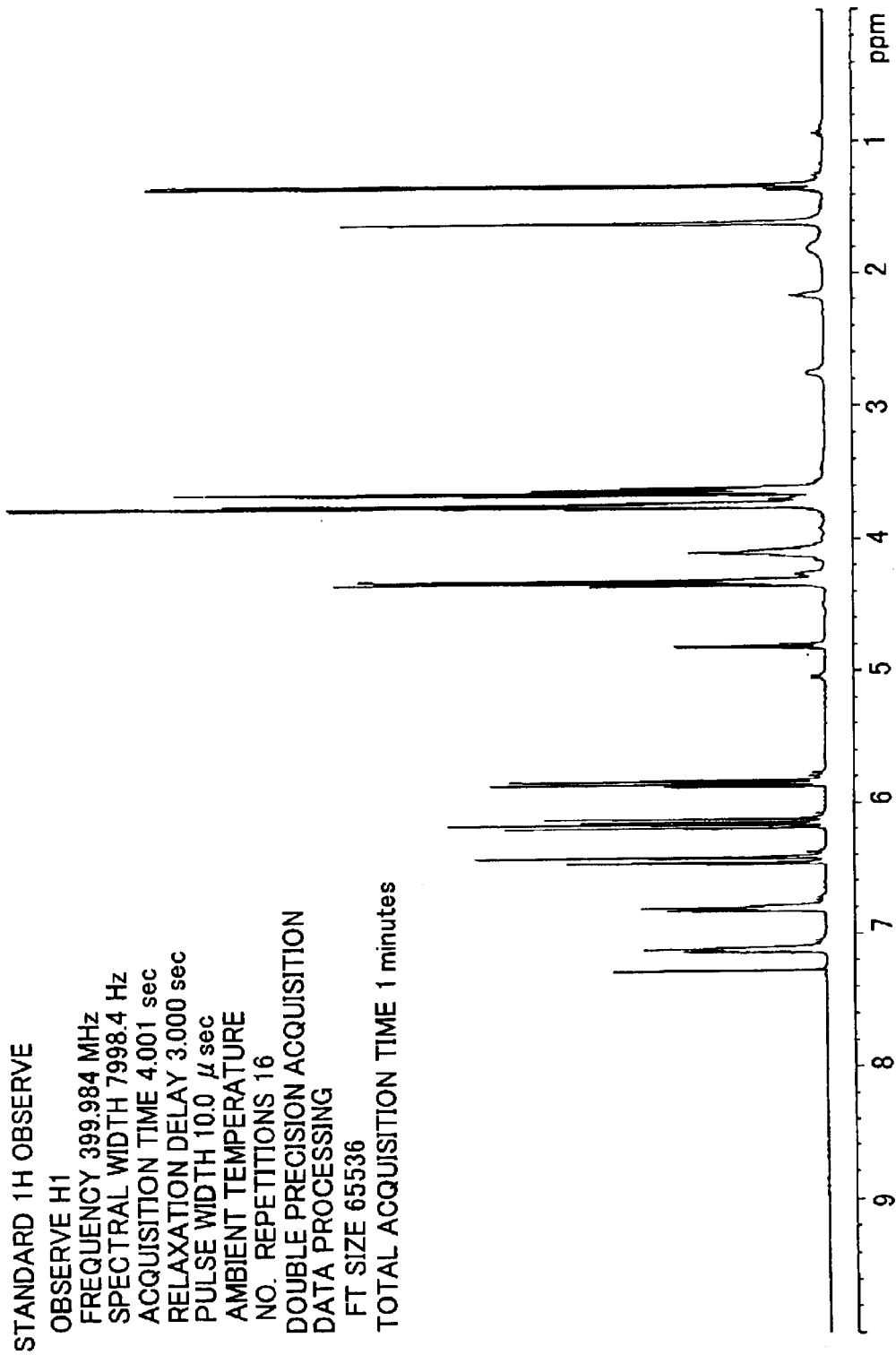
FIG. 13 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 13 shows a chart of $^1$H-NMR of the reaction product and FIG. 5 shows an IR spectrum of the product.

EXAMPLE 6

90 g (0.9 mol) of methyl methacrylate, 8.6 g (0.1 mol) of methacrylic acid, and 230 g of 2-butanone were put into a 0.5 liter flask equipped with a stirrer, a thermometer, a condenser and a nitrogen-introducing tube. After the air was sufficiently replaced by nitrogen, the temperature was raised to 70° C. Then, 0.986 g of 2,2'-azobis(2,4-dimethylvaleronitrile) dissolved in 2-butanone was introduced into the reaction mixture over 1 hour, and then polymerization was performed at 70° C. over 5 hours. 0.0017 g of hydrochloric acid was added to 98.6 g of the obtained methacrylate polymer, and the material was cooled to 10° C. in an ice bath. Thereafter, 20.02 g (0.1 mol) of VEEM was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 6:
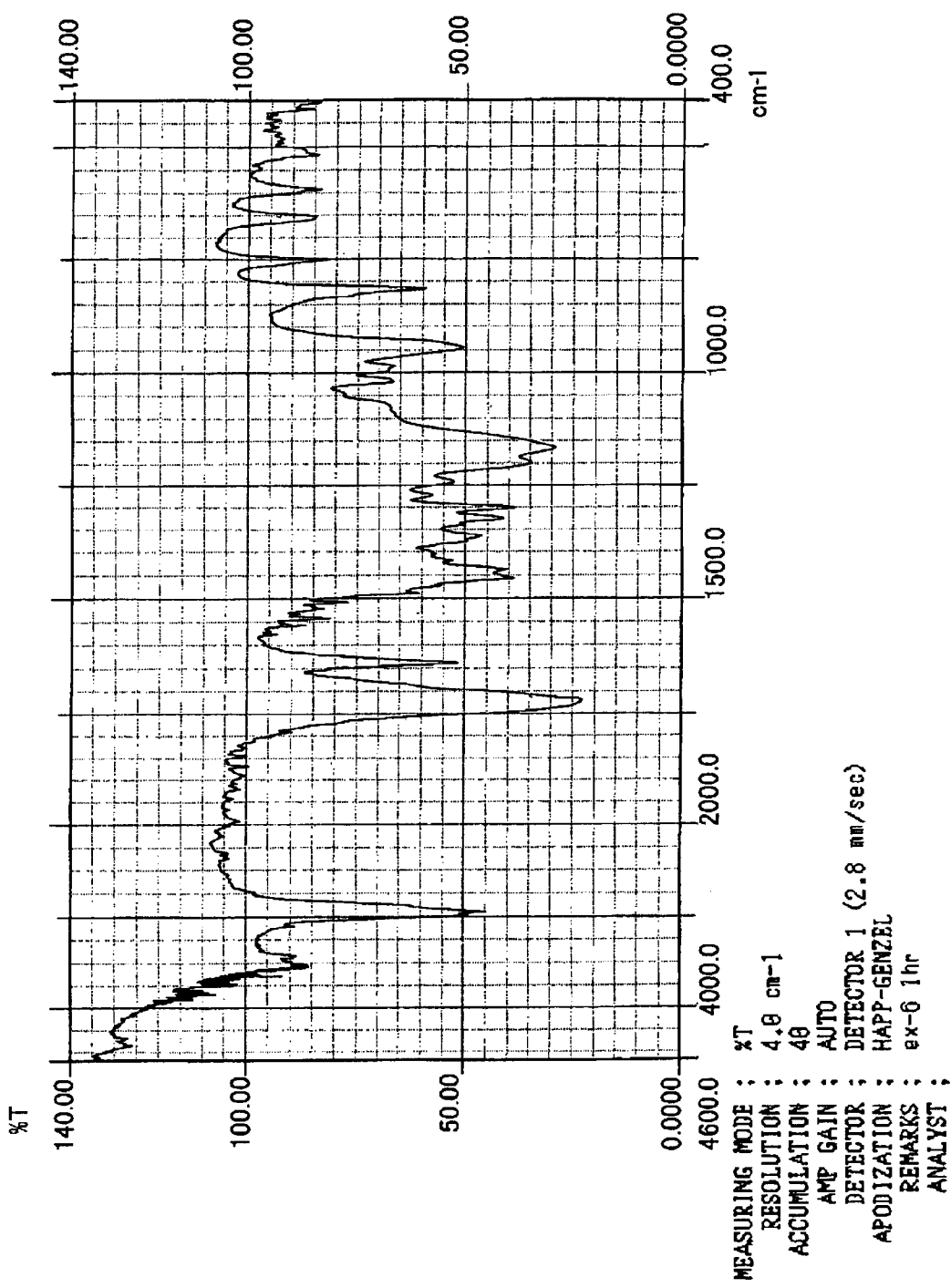
FIG. 6 shows an IR spectrum chart of a reaction product obtained from an Example.
Figure 14:
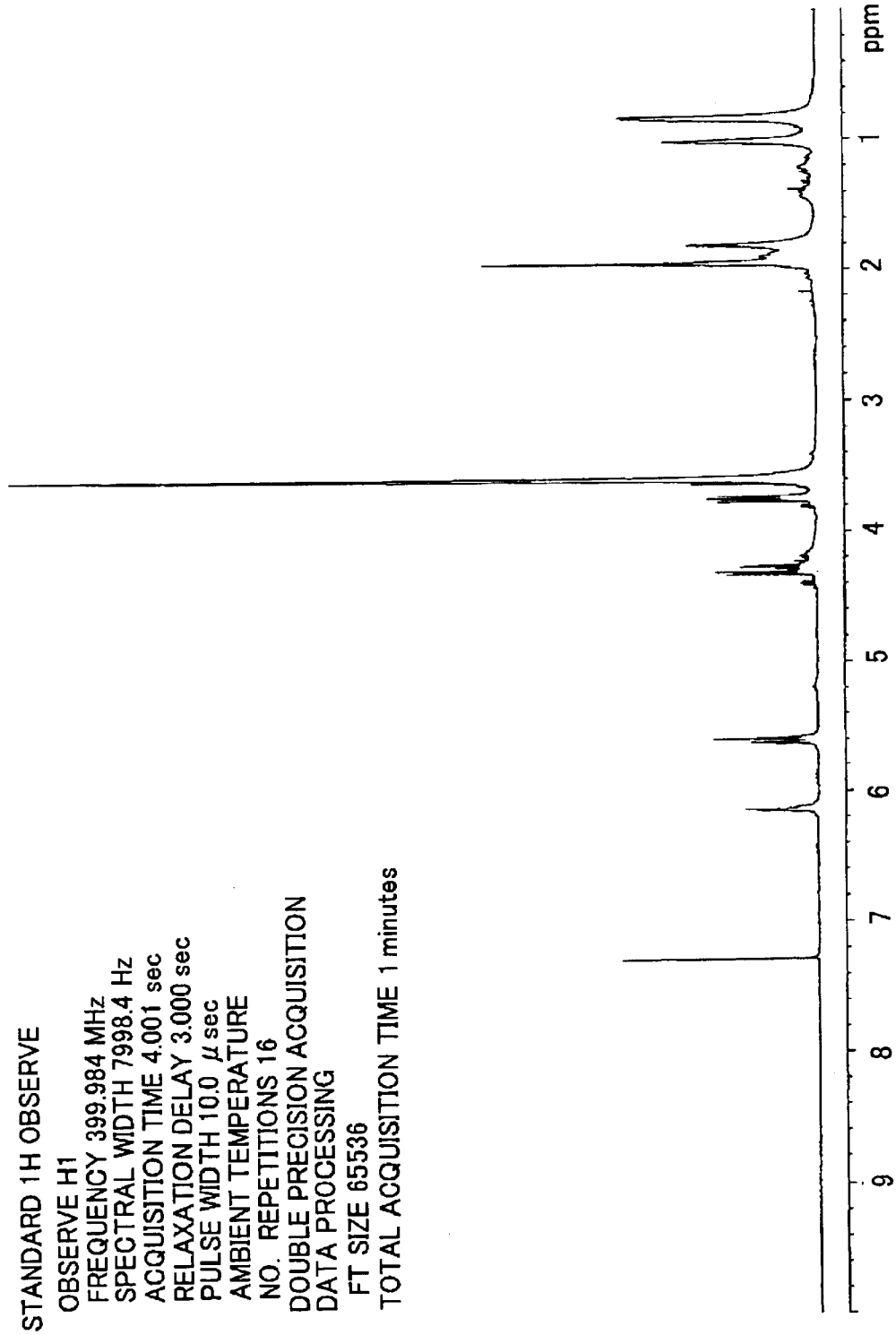
FIG. 14 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 14 shows a chart of $^1$H-NMR of the reaction product and FIG. 6 shows an IR spectrum of the product.

EXAMPLE 7

116.1 g of fumaric acid, 0.0344 g of p-toluenesulfonic acid and 488.5 g of 2-butanone were put into a 1 liter flask equipped with a stirrer, a thermometer, a condenser and a nitrogen-introducing tube, and then was cooled to 10° C. in a nice bath. Thereafter, 372.4 g (2 mol) of VEEA was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 7:
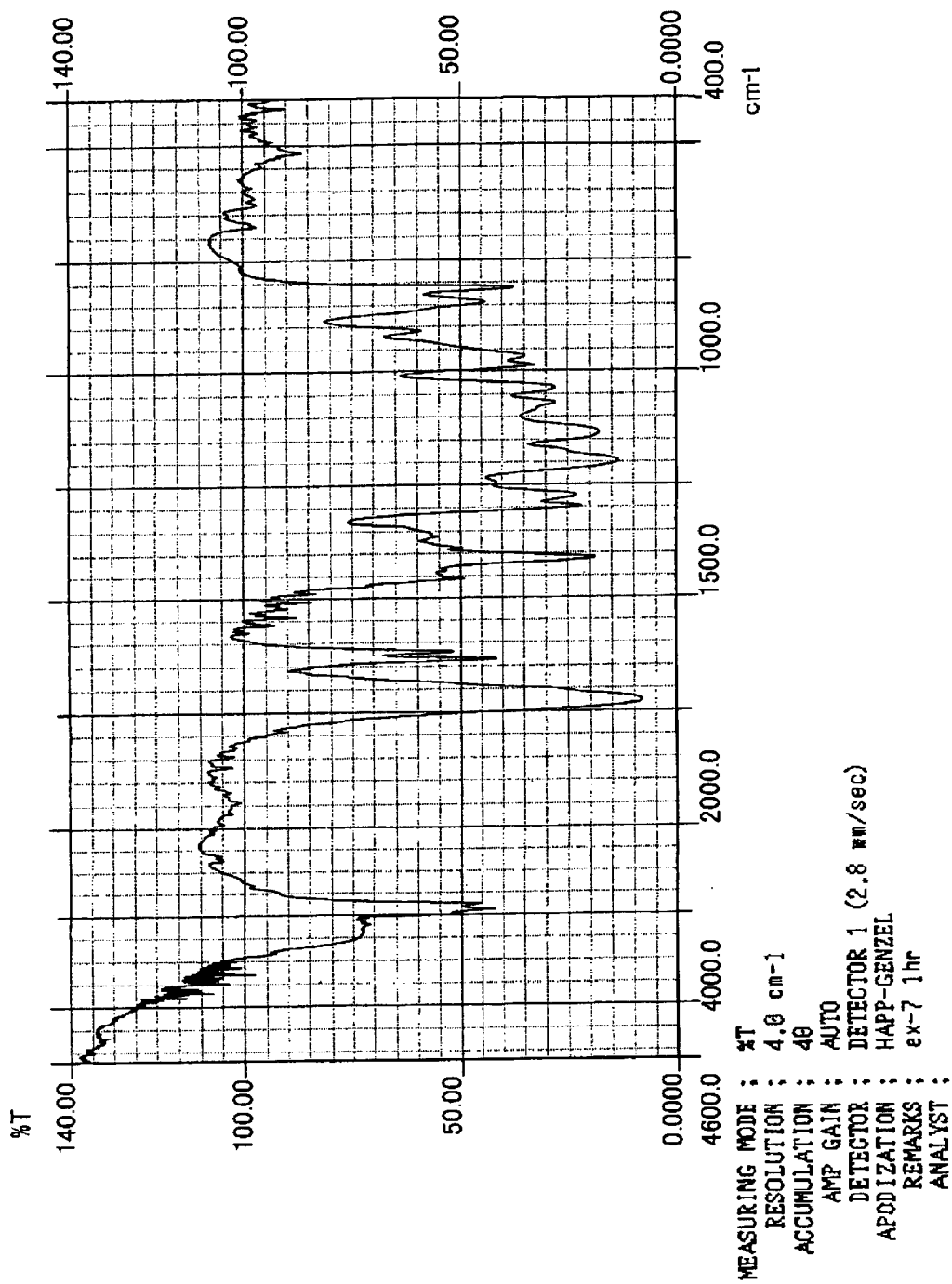
FIG. 7 shows an IR spectrum chart of a reaction product obtained from an Example.
Figure 15:
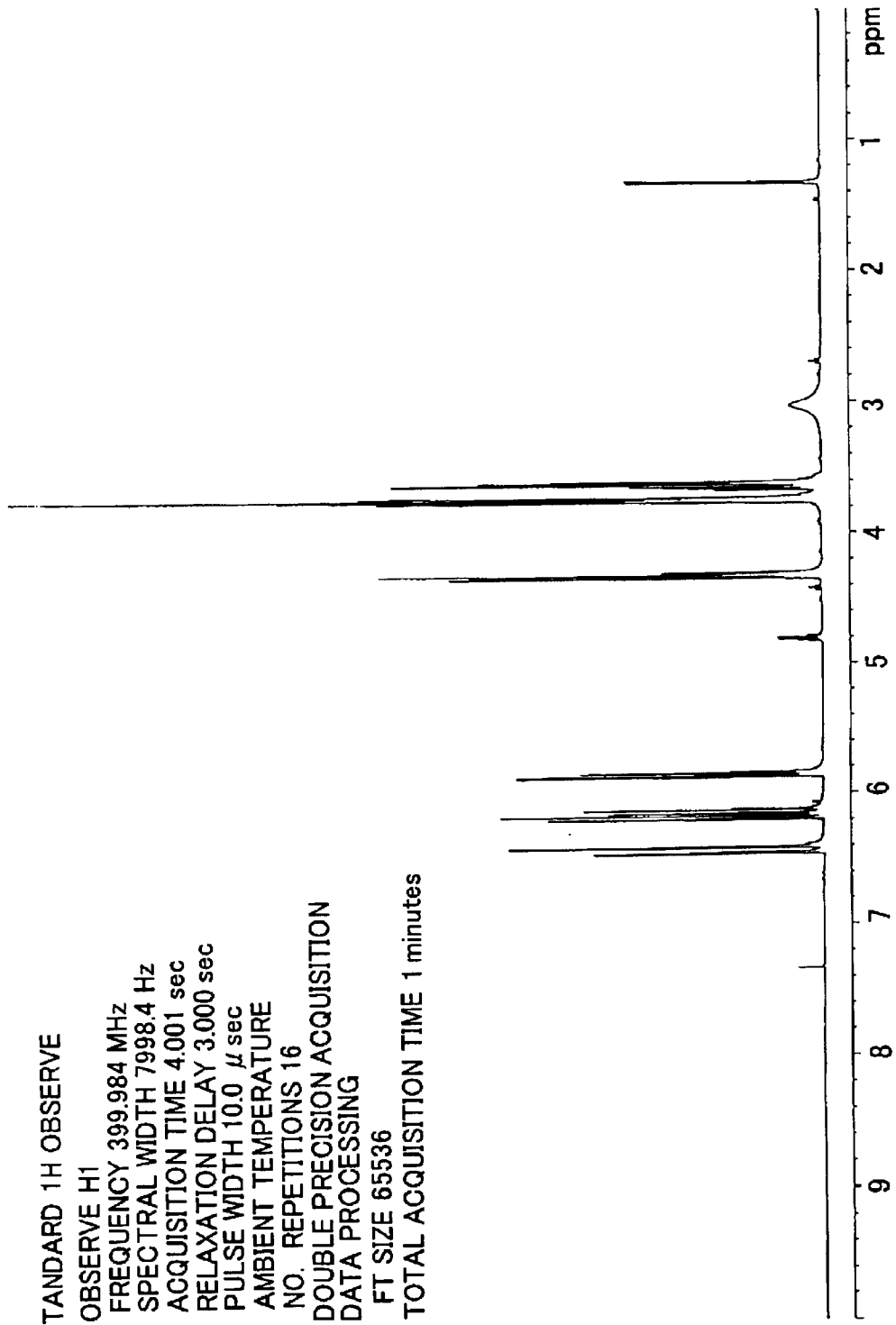
FIG. 15 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 15 shows a chart of $^1$H-NMR of the reaction product and FIG. 7 shows an IR spectrum of the product.

EXAMPLE 8

194 g (1 mol) of tetraethylene glycol and 1.46 g of hydrochloric acid were put into a 1 liter flask equipped with a stirrer, a thermometer, a condenser and a nitrogen-introducing tube, and then it was cooled to 10° C. in an ice bath. Thereafter, 372.4 g (2 mol) of VEEA was dropped and added into the resulting solution over 1 hour, and the temperature was returned to room temperature, and then the mixture was allowed to react for another two hours. The reaction solution was neutralized with a sodium hydroxide solution of 1 mol/L and was filtered, and then the reaction product was subjected to re-precipitation using n-hexane, followed by filtration and drying.

Figure 8:
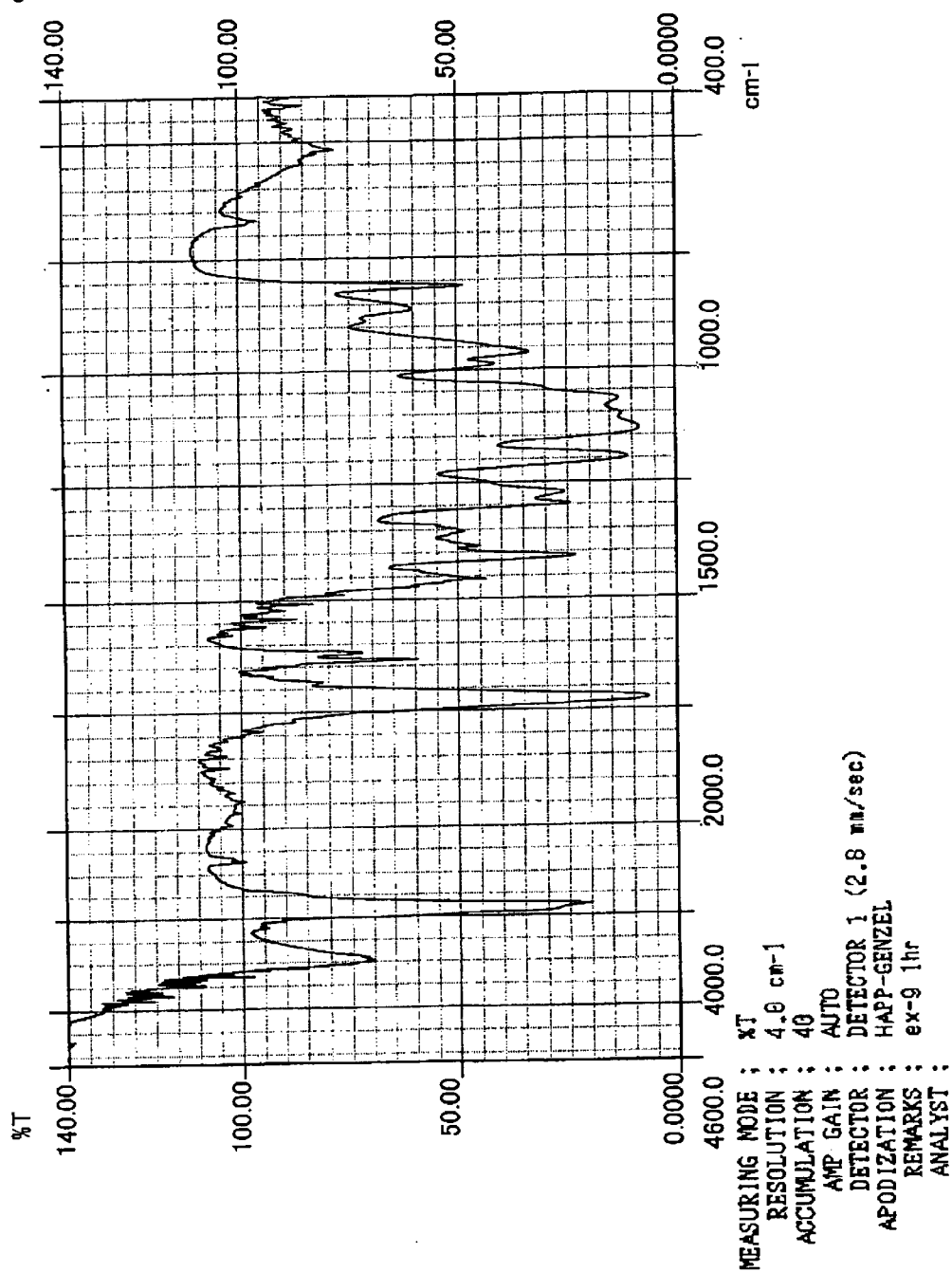
FIG. 8 shows an IR spectrum chart of a reaction product obtained from an Example.
Figure 16:
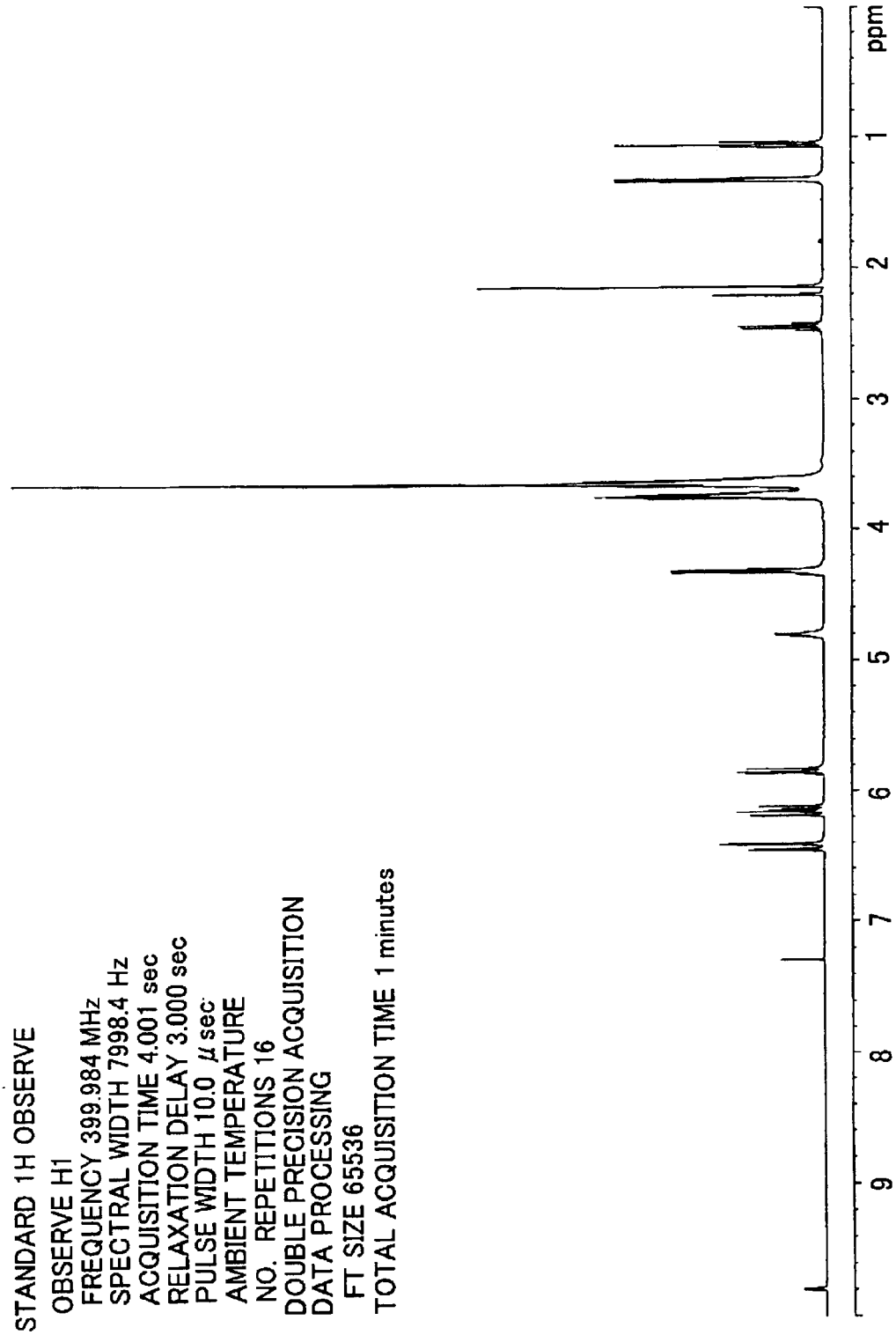
FIG. 16 is a chart of $^1$H-NMR of a reaction product obtained from an Example.

The material thus obtained was identified by means of $^1$H-NMR and IR. As a result, it was confirmed that the above-mentioned material of the reaction product is a noble compound having an acryloyl group concerning the present invention. FIG. 16 shows a chart of $^1$H-NMR of the reaction product and FIG. 8 shows an IR spectrum of the product.

EXAMPLE 9

2 parts of benzoyl peroxide were added to 100 parts by weight of the compound of Example 2 dissolved in 100 parts by weight of acetone, and the resulting solution was coated on a glass plate, and then removal of the solvent and curing were performed at 90° C. over 2 hours. The glass transition temperature of the cured material was measured by means of a differential scanning calorimeter (DSC) at a rate of temperature increase of 10° C./minute and was found to be 90° C.

Comparative Example 1

Bisphenol A epoxy resin used as a raw material in Example 2 is a liquid at normal temperature, and the glass transition temperature thereof was clearly lower than that of the cured material obtained in Example 2.

EXAMPLE 10

The glass transition temperature of the cured material made by curing the compound of Example 5 by means of a similar method as in Example 9 was determined to be 110° C.

Comparative Example 2

The glass transition temperature of the phenoxy resin itself synthesized in Example 5 was determined to be 80° C.

EXAMPLE 11

134 g (hydroxyl group=3 mol) of trimethylolpropane and 600 g (3 mol) of VEEM were put into a 1 liter flask equipped with a stirrer, a thermometer, a condenser and a nitrogen-introducing tube, and the solution was stirred and heated to 60° C. to prepare a uniform mixture solution. Thereafter, the resulting solution was cooled to 25° C. and a solution made by diluting 0.104 g of hydrochloric acid (35% aqueous solution, 0.01 mol as HCl component) with 10 g of bis(2-methoxyethyl)ether was dropped slowly into the solution while taking care of the exotherm. When the exotherm calmed down, the solution was heated to 60° C. and subjected to reaction for 4 hours. Reaction Product (1) thus obtained was analyzed using an IR spectrometer; it was found out that peak wave near 3500 $cm^{-1}$ attributable to the hydroxyl group almost disappeared.

EXAMPLE 12

263 g (hydroxyl group =about 3.5 mol) of sufficiently dehydrated polyglycerin (trademark: Polyglycerin #750, product of Sakamoto Yakuhin Kogyo Co., Ltd.) and 700 g (3.5 mol) of VEEM were put into a 1 liter flask equipped with a stirrer, a thermometer, a condenser and a nitrogen-introducing tube, and the solution was stirred. At 25° C., a solution made by diluting 1.1 g of hydrochloric acid (35% aqueous solution, 0.011 mol as HCl component) with 10 g of bis (2-methoxyethyl)ether was dropped slowly into the solution while taking care of the exotherm. When the exotherm calmed down, the solution was heated to 60° C. and subjected to reaction for 4 hours. Reaction Product (2) thus obtained was analyzed using an IR spectrometer; it was found out that peak wave near 3500 $cm^{-1}$ attributable to the hydroxyl group almost disappeared.

EXAMPLE 13

50 g (0.5 mol) of methyl methacrylate, 65.1 g (0.5 mol) of 2-hydroxyethyl methacrylate, and 173.5 g of bis-ether (2-methoxyethyl) were put into a 0.5 liter flask equipped with a stirrer, a thermometer, a condenser and a nitrogen-introducing tube. After the air was sufficiently replaced by nitrogen, the temperature was raised to 70° C. Thereafter, 0.61 g of n-dodecylmercaptan was charged into the solution, then a solution prepared by dissolving 0.58 g of 2,2'-azobis (2,4-dimethylvaleronitrile) in bis-ether (2-methoxyethyl) was charged to the resulting system over one hour and polymerization was performed at 70° C. over 5 hours. To 289 g of the mixture solution of the methacrylic polymer and bis(2-methoxyethyl)ether thus obtained, 0.17 g of 4-hydroxy-2,2,6,6-tetramethylpiperidinoxyl and 50 g (0.25 mol) of VEEM as inhibitors were added and stirred. At 25° C., a solution made by diluting 0.078 g of hydrochloric acid (35% aqueous solution, 7.5×$10^{-4}$ mol as HCl component) with 10 g of bis-ether (2-methoxyethyl) was slowly dropped into the system while taking care of the exotherm. When the exotherm calmed down, the solution was heated to 60° C. and subjected to reaction for 6 hours. A curable resin solution thus obtained was analyzed using an IR spectrometer; it was confirmed that the intensity of peak wave near 3500 $cm^{-1}$ attributable to the hydroxyl group was reduced. 339 g of the mixture solution of a polymer and bis(2-methoxyethyl)ether thus obtained, 38 g (0.25 mol) of tetrahydrophthalic anhydride and 1.51 g of tetraphenylphosphonium bromide were mixed, and then an acid anhydride addition reaction to the hydroxyl group was performed at 100° C. over 4 hours under a mixed gas atmosphere. The acid value of Curable Resin Solution (3) thus obtained was determined to be 37 mg KOH/g.

EXAMPLE 14

60 g (0.6 mol) of methyl methacrylate, 28.8 g (0.4 mol) of methacrylic acid, and 134.1 g of bis-ether (2-methoxyethyl) were put into a 0.5 liter flask equipped with a stirrer, a thermometer, a condenser and a nitrogen-introducing tube. After the air was sufficiently replaced by nitrogen, the temperature was raised to 70° C. Thereafter, 0.61 g of n-dodecylmercaptan was charged into the solution, and a solution prepared by dissolving 0.45 g of 2,2'-azobis (2,4-dimethylvaleronitrile) in bis (2-methoxyethyl)ether was charged over one hour into the resulting system and polymerization was performed at 70° C. over 5 hours. To 224 g of the mixture solution of the methacrylic polymer and bis-ether (2-methoxyethyl) thus obtained, 0.13 g of 4-hydroxy-2,2,6,6-tetramethylpiperidinoxyl and 40 g (0.2 mol) of VEEM as inhibitors were added and stirred. At 25° C., a solution made by diluting 0.063 g of hydrochloric acid (35% aqueous solution, 6×$10^{-4}$ mol as HCl component) with 10 g of bis(2-methoxyethyl)ether was slowly dropped into the system while taking care of exotherm. When the exotherm calmed down, the solution was heated to 60° C. and subjected to reaction for 3 hours. The acid value of Curable Resin Solution (4) thus obtained was determined to be 43 mg KOH/g.

EXAMPLES 15 TO 18

A photo-curable resin composition was prepared using each reaction product and curable resin solution obtained in Example 11 to 14 on the basis of a composition (parts by weight) as shown in Table 1 and was evaluated by the methods below for thermal decomposition properties, solvent developability and alkali developability. The results are given in Table 2.

Comparative Examples 3 to 4

60 g (0.6 mol) of methyl methacrylate, 28.8 g (0.4 mol) of methacrylic acid, and 134.1 g of bis(2-methoxyethyl) ether were put into a 0.5 liter flask equipped with a stirrer, a thermometer, a condenser and a nitrogen-introducing tube. After the air was sufficiently replaced by nitrogen, the temperature was raised to 70° C. Thereafter, 0.61 g of n-dodecylmercaptan was charged into the solution, and then a solution prepared by dissolving 0.45 g of 2,2'-azobis(2,4-dimethylvaleronitrile) in bis(2-methoxyethyl)ether was charged into the resulting system over one hour and polymerization was performed at 70° C. over 5 hours. To 224 g of the mixture solution of the methacrylic polymer and bis(2-methoxyethyl)ether thus obtained, 0.13 g of 4-hydroxy-2,2,6,6-tetramethylpiperidinoxyl as an inhibitor and 1.01 g of tetraphenylphosphonium bromide as esterification catalysts and 28.4 g (0.2 mol) of glycidyl methacrylate were added and stirred. Then the solution was subjected to reaction at 110° C. for 4 hours. The acid value of Curable Resin Solution (5) thus obtained was determined to be 45 mg KOH/g.

A photo-curable resin composition was prepared using thus obtained Curable Resin Solution (5) on the basis of a composition (parts by weight) as shown in Table 1 and was evaluated by the methods below for thermal decomposition properties, solvent developability and alkali developability. The results are given in Table 1.

TABLE 1

|  | Examples | | | | Comparative Examples | |
|---|---|---|---|---|---|---|
|  | 15 | 16 | 17 | 18 | 3 | 4 |
| Composition of photo-curable paste composition (parts by mass) | | | | | | |
| Reaction product (1) | 21 | — | — | — | — | — |
| Reaction product (2) | — | 21 | — | — | — | — |
| Curable resin solution (3) | — | — | 100 | — | — | — |
| Curable resin solution (4) | — | — | — | 100 | — | — |
| Curable resin solution (5) | — | — | — | — | — | 100 |
| TMPTMA | — | — | — | — | 21 | — |
| PMMA | 49 | 49 | — | — | 49 | — |
| Bis(2-methoxyethyl)ether | 30 | 30 | — | — | 30 | — |

In Table 1, "TMPTMA" refers to trimethylolpropane trimethacrylate and "PMMA" means polymethyl methacrylate (number average molecular weight =35,000, weight average molecular weight=50,000).

TABLE 2

|  | Examples | | | | Comparative Examples | |
|---|---|---|---|---|---|---|
|  | 15 | 16 | 17 | 18 | 3 | 4 |
| Thermal decomposition (Temperature for the mass reduction ratio to be 98% [° C.]) | 420 | 432 | 435 | 440 | 485 | 490 |
| Solvent developability | ○ | ○ | ○ | — | ○ | — |
| Alkali developability | — | — | — | ○ | — | ○ |

Evaluation Methods
[Thermal Decomposition Properties]

5 parts of Irgacure 907 (product of Ciba Specialty Chemicals Co., Ltd.) were added to 100 parts of the components, excluding solvent, in each photo-curable composition and the resulting material was applied on a glass plate in a thickness of 20 to 30 μm, and then was dried at 80° C. for 1 hour in a hot-air circulation type drying oven. The plate was covered with a transparent film and was irradiated with light with a light quantity of 2000 mJ/cm² using a 250 W super high-pressure mercury lamp to yield a cured coating. The thermal decomposition properties of this cured coating were studied by TGA (Thermal Gravity Analysis, product of Mac Science Corp., TG-DTA 2000). The coating was heated from 25° C. to 500° C. at a rate of temperature increase of 20° C./minute under an air atmosphere to measure the temperature for the weight reduction ratio to be 98%.

[Solvent Developability]

Each photo-curable composition was applied on a copper plate in a thickness of 20 to 30 μm, and then was dried at 80° C. for 1 hour in a hot-air circulation type drying oven to thereby obtain a coating. Thereafter, the development was carried out using propylene glycol monomethyl ether acetate at 30° C. for 60 seconds. Then the remaining coating was visually evaluated.

○: the coating was completely developed; Δ: an adhesive slightly remained; X: an adhesive remained in quantity.

[Alkali Developability]

Each photo-curable composition was applied on a copper plate in a thickness of 20 to 30 μm, and then was dried at 80° C. for 1 hour in a hot-air circulation type drying oven to thereby obtain a coating. Thereafter, the development was carried out using a 1% $Na_2CO_3$ aqueous solution at 30° C. for 60 seconds. Then the remaining coating was visually evaluated.

○: the coating was completely developed; Δ: an adhesive slightly remained; X: an adhesive remained in quantity.

EXAMPLES 19 TO 24

A composition formulated according to a formulation composition (parts by mass) in Table 3 was kneaded with a ceramic triple roll to obtain a photo-curable paste composition. This composition was applied on a copper plate in a thickness of 20 to 30 μm, and then was dried at 80° C. for 1 hour in a hot-air circulation type drying oven to thereby obtain a coating. The coating thus obtained was covered with a pattern film and was irradiated with light with a light quantity of 2000 mJ/cm² using a 250 W super high-pressure mercury lamp. Then, each coating was developed at 30° C. for 60 seconds using a developer as shown in Table 3, and subsequently was fired for 10 minutes at a baking temperature (600 to 800° C.) as shown in Table 3. The line pattern thus obtained was visually evaluated.

○: the contrast between the light exposed portion and the light un-exposed portion was clearly distinguished and no broken lines, short lines, or the like were present; Δ the etching of the light exposed portion was insufficient; X: etching was unable or the whole was melted.

The results are summarized in Table 3.

TABLE 3

|  | Examples | | | | | |
|---|---|---|---|---|---|---|
|  | 19 | 20 | 21 | 22 | 23 | 24 |
| Preparation composition (parts by mass) Curable-resin | | | | | | |
| Photo-curable resin composition of Example 15 | 100 | 100 | — | — | — | — |
| Photo-curable resin composition of Example 16 | — | — | 100 | 100 | — | — |
| Photo-curable resin composition of Example 18 | — | — | — | — | 100 | 100 |
| Inorganic powder | | | | | | |
| Glass frit | 140 | — | 140 | — | 140 | — |
| Silver powder | — | 210 | — | 210 | — | 210 |
| Irgacure 907 | 3.5 | 3.5 | 3.5 | 3.5 | 3 | 3 |
| Baking temperature (° C.) | 600 | 800 | 600 | 800 | 600 | 800 |

TABLE 3-continued

|  | Examples | | | | | |
| --- | --- | --- | --- | --- | --- | --- |
|  | 19 | 20 | 21 | 22 | 23 | 24 |
| Estimation of line forming | ○ | ○ | ○ | ○ | ○ | ○ |
| Developer | 1 | 1 | 1 | 1 | 2 | 2 |

In Table 3, "glass frit" is $ZnO/PbO/B_2O_3/SiO_2$-based glass frit and "Irgacure 907" is a photo polymerization initiator, product of Ciba Specialty Chemicals Co., Ltd. In addition, "1" in the "developer" section refers to developer 1, propylene glycol monomethyl ether acetate, and "2" means developer 2, a 1% $Na_2CO_3$ aqueous solution.

EXAMPLE 25

A reactor equipped with a stirrer, a condenser, a nitrogen-introducing tube and a thermometer was charged with 438 parts of a cresol novolac type epoxy resin "EOCN-104S" (product of Nippon Kayaku Co., Ltd., epoxy equivalent 219), 144 parts of acrylic acid, 313 parts of propylene glycol monomethyl ether acetate, 2.9 parts of triphenylphosphine as an esterification catalyst, and 0.5 part of methylhydroquinone as a polymerization inhibitor, and a reaction was carried out at 110° C. for 10 hours. The acid value of the reaction product was made sure to be 5 mg KOH/g. Thereafter, 60 parts of propylene glycol monomethyl ether acetate, 112 parts of VEEA, 0.2 part of hydrochloric acid as an addition reaction catalyst, and 0.6 part of 4-hydroxy-2,2,6,6-tetramethylpiperidine-N-oxyl as a polymerization inhibitor were added thereto, and a reaction was performed at 40° C. for 1 hour. Then, 0.3 part of glycidylmethacrylate was added thereto, and deactivation treatment of hydrochloric acid was conducted at 40° C. for 1 hour to obtain a mixture [Curable Resin Solution (6)] containing propylene glycol monomethyl ether acetate and 65% of a resin of the present invention.

EXAMPLE 26

To 500 parts of the Curable Resin Solution (6) obtained in Example 25 were added 41 parts of propylene glycol monomethyl ether acetate and 76 parts of tetrahydrophthalic anhydride and a reaction was carried out at 100° C. for 5 hours to thereby obtain a mixture [Curable Resin Solution (7)] containing propylene glycol monomethyl ether acetate and 65% of a resin with an acid value of 77 mg KOH/g of the present invention.

EXAMPLE 27

A reactor same as in Example 25 was charged with 438 parts of a cresol novolac type epoxy resin "EOCN-104S", 83 parts of p-hydroxyphenyl-2-ethanol, 101 parts of acrylic acid, 335 parts of propylene glycol monomethyl ether acetate, 3.1 parts of triphenylphosphine as an esterification catalyst, and 0.7 part of 4-hydroxy-2,2,6,6-tetramethylpiperidine-N-oxyl as a polymerization inhibitor and a reaction was carried out at 110° C. for 12 hours. The acid value of the reaction product was made sure to be 6 mg KOH/g. Thereafter, 60 parts of propylene glycol monomethyl ether acetate, 112 parts of VEEA, and 0.2 part of hydrochloric acid as an addition reaction catalyst were added and a reaction was performed at 40° C. for 1 hour. Then, 0.3 part of glycidylmethacrylate was added thereto, and deactivation treatment of hydrochloric acid was conducted at 40° C. for 1 hour. Subsequently, 93 parts of propylene glycol monomethyl ether acetate were added thereto, and a reaction was carried out at 100° C. for 5 hours to thereby obtain a mixture [Curable Resin Solution (8)] containing propylene glycol monomethyl ether acetate and 65% of a resin with an acid value of 77 mg KOH/g of the present invention.

EXAMPLE 28

A reactor same as in Example 25 was charged with 400 parts of a cresol novolac type epoxy resin "SUMI-EPOXY ESCN195XHH", 144 parts of acrylic acid, 293 parts of propylene glycol monomethyl ether acetate, 0.5 part of chromium bromide hexahydrate as an esterification catalyst, and 0.7 part of 4-hydroxy-2,2,6,6-tetramethylpiperidine-N-oxyl as a polymerization inhibitor and a reaction was carried out at 110° C. for 9 hours. The acid value of the reaction product was made sure to be 4 mg KOH/g. Thereafter, 60 parts of propylene glycol monomethyl ether acetate, 112 parts of VEEA, and 0.2 part of hydrochloric acid as an addition reaction catalyst were added and a reaction was performed at 40° C. for 1 hour. Then, 0.3 part of glycidyl methacrylate was added thereto, and deactivation treatment of hydrochloric acid was conducted at 40° C. for 1 hour. Subsequently, 111 parts of propylene glycol monomethyl ether acetate, 206 parts of tetrahydrophthalic anhydride, and 1 part of triphenylphosphine as an esterification catalyst were added thereto, and a reaction was carried out at 100° C. for 5 hours. Then, to this resulting solution were added 23 parts of propylene glycol monomethyl ether acetate and 42 parts of a bisphenol A type epoxy resin "EPO TOHTO YD-127" (product of Tohto Kasei Co., Ltd., epoxy equivalent 184), and a reaction was conducted at 110° C. for 5 hours to elongate the chain, thereby a mixture [Curable Resin Solution (9)] containing propylene glycol monomethyl ether acetate and 65% of a resin with an acid value of 74 mg KOH/g of the present invention.

EXAMPLES 29 TO 34

A photo-curable composition was prepared using each curable resin solution obtained in above Examples 25 to 28 according to a formulation composition in Table 4 and was evaluated by the following methods. The results are shown in Table 5.

Comparative Examples 5 and 6

A reactor same as in Example 25 was charged with 438 parts of a cresol novolac type epoxy resin "EOCN-104S", 144 parts of acrylic acid, 313 parts of propylene glycol monomethyl ether acetate, 2.9 parts of triphenylphosphine as an esterification catalyst, and 0.5 part of 4-hydroxy-2,2,6,6-tetramethylpiperidine-N-oxyl as a polymerization inhibitor and a reaction was carried out at 110° C. for 10 hours. The acid value of the reaction product was made sure to be 5 mg KOH/g. Then, 73 parts of propylene glycol monomethyl ether acetate and 136 parts of tetrahydrophthalic anhydride were added thereto and a reaction was performed at 100° C. for 5 hours, thereby obtaining a mixture [Curable Resin Solution (10)] containing propylene glycol monomethyl ether acetate and 65% of a resin with an acid value of 78 mg KOH/g.

A photo-curable composition was prepared using the obtained Curable Resin Solution (10) according to a formulation composition in Table 4 and was evaluated by the following methods. The results are shown in Table 5.

coated laminated plate with a thickness of 1.6 mm and was dried at 80° C. for 30 minutes in a hot-air circulation type drying oven to form a film. Then, a stofer 21-stage step tablet was made close to the film, which was irradiated with light with a quantity of light of 500 mJ/cm$^2$ by means of a 1 kW ultra-high pressure mercury lamp. The film was developed under the same conditions as in evaluations of developability and the step number of the remaining step tablet was checked.

[Solder Heat Resistance]

A dried film was formed as in the exposure sensitivity evaluations. Then, a solder mask pattern film was made close to the film, which was irradiated with light with a quantity of light of 500 mJ/cm$^2$ by means of a 1 kW ultra-high pressure mercury lamp. The film was developed under the same conditions as in evaluations of developabil-

TABLE 4

|  | Examples | | | | | | Comparative Examples | |
|---|---|---|---|---|---|---|---|---|
|  | 13 | 30 | 31 | 32 | 33 | 34 | 5 | 6 |
| Curable resin solution (90 parts by mass) | (6) | (7) | (7) | (8) | (9) | (9) | (10) | (10) |
| Diluent:Multifunctional monomer | 10 | 10 | 10 | 10 | 10 | 10 | 10 | 10 |
| Pentaerythritol tetraacrylate | | | | | | | | |
| Diluent:Solvent | 20 | 20 | 20 | 20 | 20 | 20 | 20 | 20 |
| Propylene glycol monomethyl ether acetate | | | | | | | | |
| Photo polymerization initiator:Irgacure 907 | 8 | 8 | 8 | 8 | 8 | 8 | 8 | 8 |
| Epoxy resin:YDPN-638P | 0 | 20 | 0 | 20 | 20 | 0 | 20 | 0 |
| Oxazoline compound: | 0 | 0 | 20 | 0 | 0 | 20 | 0 | 20 |
| 1,3-phenylen bis (2-oxazoline) | | | | | | | | |
| Curing agent:Dicyandiamide | 2 | 2 | 2 | 2 | 2 | 2 | 2 | 2 |
| Filler:Barium sulfate | 30 | 30 | 30 | 30 | 30 | 30 | 30 | 30 |
| Anti-forming agent:Floren AC300 | 1.2 | 1.2 | 1.2 | 1.2 | 1.2 | 1.2 | 1.2 | 1.2 |
| Pigment:Phthalocyanine green | 0.6 | 0.6 | 0.6 | 0.6 | 0.6 | 0.6 | 0.6 | 0.6 |

In the following, descriptions in Table 4 are explained. Each numeric value in Table 4 has units of parts by mass. "Irgacure 907" is a photo polymerization initiator, a product of Ciba Specialty Chemicals Co., Ltd., "YDPN-638P" is a phenol novolac type epoxy, a product of Tohto Kasei Co., Ltd., and "Floren AC300" is an antifoaming agent, product of KYOEISYA CHEMICAL Co., Ltd.

[Developability-1]

Each photo-curable composition was applied in a thickness of 20 to 30 μm on a degreased and cleaned, copper-coated laminated plate with a thickness of 1.6 mm and was dried at 80° C. for a specified time in a hot-air circulation type drying oven to obtain a film. Then, each was developed at 30° C. for 90 seconds under pressure of 2.06×10$^{-1}$ MPa using propylene glycol monomethyl ether acetate and evaluation was made visually on the remaining resin. ○: the film was completely developed; Δ: a deposit slightly remained; X: a deposit remained in quantity.

[Developability-2]

Each photo-curable composition was applied in a thickness of 20 to 30 μm on a degreased and cleaned, copper-coated laminated plate with a thickness of 1.6 mm and was dried at 80° C. for a specified time in a hot-air circulation type drying oven to obtain a film. Then, each was developed at 30° C. for 90 seconds under pressure of 2.06×10$^{-1}$ MPa using a 1% Na$_2$CO$_3$ aqueous solution and evaluation was made visually on the remaining resin. ○: the film was completely developed; Δ: a deposit slightly remained; X: a deposit remained in quantity.

[Exposure Sensitivity]

Each photo-curable composition was applied in a thickness of 20 to 30 μm on a degreased and cleaned, copperity and the un-exposed portion was dissolved and removed, and then the film was further heated at 150° C. for 30 minutes to thereby obtain a cured film. Thereafter, the film obtained was immersed in a solder bath of 260° C. for 20 seconds in accordance with the JIS D-0202 Test Method and then the state of the film was evaluated after the immersion. ○: abnormalities were not observed in the appearance of the film; X: swelling, melting or peeling was observed in the appearance of the film.

[Electroless Gold Plating Resistance]

A cured film was obtained as in the case of solder heat resistance evaluations. Thereafter, gold plating was performed in a current density of 1 A/dm$^2$ for 15 minutes using "AUTRONEX CI" (gold plating solution available from Sel-Rex Corp., USA), and then the film was subjected to a peeling test by means of an adhesive tape to visually evaluate the peeling state. ○: no peeling occurred; Δ: peeling slightly occurred; X: 20% or more of the whole area was peeled.

[PCT Resistance]

A cured film was obtained as in the case of solder heat resistance evaluations. Then, the appearance of the film was visually evaluated after the film was placed at 121° C. at atmospheric pressure of 2.03×10$^2$ kPa under a saturated vapour atmosphere for 168 hours. ○: abnormalities were not observed in the appearance of the film; X: swelling, melting or peeling was observed in the appearance of the film.

TABLE 5

|  | Examples | | | | | | Comparative Examples | |
|---|---|---|---|---|---|---|---|---|
|  | 29 | 30 | 31 | 32 | 33 | 34 | 5 | 6 |
| Developability-1 | | | | | | | | |
| Drying time 30 min | ○ | — | — | — | — | — | — | — |
| Drying time 60 min | ○ | — | — | — | — | — | — | — |
| Developability-2 | | | | | | | | |
| Drying time 30 min | — | ○ | ○ | ○ | ○ | ○ | ○ | ○ |
| Drying time 60 min | — | ○ | ○ | ○ | ○ | ○ | Δ | X |
| Exposure sensitivity | 8 | 8 | 8 | 8 | 9 | 9 | 6 | 6 |
| Solder heat resistance | ○ | ○ | ○ | ○ | ○ | ○ | ○ | ○ |
| Electroless gold plating resistance | ○ | ○ | ○ | ○ | ○ | ○ | X | Δ |
| PCT resistance | ○ | ○ | ○ | ○ | ○ | ○ | X | X |

EXAMPLES 35 TO 44

Into a four-necked flask fitted with an agitation device, a thermometer, a purifying column and a nitrogen-introducing tube were charged 200 parts of succinic anhydride, 600 parts of polyethylene glycol #600, and 0.8 part of triethyl benzyl ammonium chloride. The mixture was gradually heated to 100° C. in a flow of nitrogen and then was subjected to a reaction for 5 hours at the temperature to give a carboxyl group-containing compound (1).

Into a four-necked flask fitted with an agitation device, a thermometer, a purifying column and a gas-introducing tube was charged each raw material in a formulation as shown in Table 6 and 7. The resulting material was heated in a flow of air to a temperature as indicated in Table 6 and 7. Thereafter, 0.01 part of hydrochloric acid diluted to 1% with bis(2-methoxyethyl)ether was slowly dropped into 100 parts of a raw material and the resulting material was subjected to an addition reaction at each temperature for 5 hours. Decreases in the amount of hydroxyl groups and carboxyl groups were confirmed by means of IR spectrum and the acid value, respectively. As a result, compounds (11) to (20) having a (meth)acryloyl group were obtained.

TABLE 6

|  | Examples | | | |
|---|---|---|---|---|
|  | 35 | 36 | 37 | 38 |
| Reaction product | (11) | (12) | (13) | (14) |
| VEEA | 372 | — | 372 | — |
| VEEM | — | 400 | — | 400 |
| TEG | 194 | 194 | — | — |
| Compound (1) containing carboxyl group | — | — | 800 | 800 |
| Reaction temperature (° C.) | 40 | 40 | 40 | 40 |
| Molecular weight (calculated value) of obtained compound | 566 | 594 | 1172 | 1200 |

TABLE 7

|  | Examples | | | | | |
|---|---|---|---|---|---|---|
|  | 39 | 40 | 41 | 42 | 43 | 44 |
| Reaction product | (15) | (16) | (17) | (18) | (19) | (20) |
| Polyglycerin | 750 | 750 | — | — | — | — |
| Sorbitol | — | — | 182 | 182 | — | — |
| TMP-30EO | — | — | — | — | 1452 | 1452 |
| VEEA | 744 | — | 558 | — | 558 | — |
| VEEM | — | 800 | — | 600 | — | 600 |
| Reaction temperature (° C.) | 40 | 40 | 100 | 100 | 70 | 70 |
| Molecular weight (calculated value) of obtained compound | 1494 | 1550 | 740 | 782 | 2012 | 2054 |

EXAMPLES 45 TO 54

The obtained compound (11) to (20) having a (meth)acryloyl group, deionized water, a coloring agent and a photo polymerization initiator was mixed in a formulation as shown in Table 8 and 9 and was sufficiently mixed using a stirrer to obtain an aqueous photo-curable composition. 25 g of this composition was placed in a 50 ml glass container and was allowed to stand to observe the stability of dissolution of the coloring agent. ○: no separation occurred within 30 minutes after quiet standing; X: separation occurred within 30 minutes.

Then, this composition was applied on a piece of copy paper using a No.18 bar coater and then was cured by a UV irradiation apparatus (250 W super-high pressure mercury lamp) using a power of 1 J/cm². The copy paper having the composition applied thereon was immersed in water at 25° C. for 1 minute and then was visually evaluated for the degree of color fading. ○: color was not changed at all; Δ: a bit of color fading occurred; X: almost no color remained. These evaluations are compared with those of polyethylene glycol diacrylate with as shown in Comparative Examples. These results are summarized in Tables 8 and 9.

TABLE 8

|  | Examples | | | |
|---|---|---|---|---|
|  | 45 | 46 | 47 | 48 |
| Reaction product | (11) | (12) | (13) | (14) |
| Molecular weight (calculated value) | 566 | 594 | 1172 | 1200 |
| Addition level | 30 | 30 | 30 | 30 |
| Deionized water | 70 | 70 | 70 | 70 |
| Irgacure 2959 | 0.5 | 0.5 | 0.5 | 0.5 |
| Benzopurpurine 4B | 5 | 5 | 5 | 5 |
| Stability of dissolution | ○ | ○ | ○ | ○ |
| Water resistance of cured material | ○ | ○ | Δ | Δ |

TABLE 9

|  | Examples | | | | | |
|---|---|---|---|---|---|---|
|  | 49 | 50 | 51 | 52 | 53 | 54 |
| Reaction product | (15) | (16) | (17) | (18) | (19) | (20) |
| Molecular weight (calculated value) | 1494 | 1550 | 740 | 782 | 2012 | 2054 |
| Addition level | 30 | 30 | 30 | 30 | 30 | 30 |
| Deionized water | 70 | 70 | 70 | 70 | 70 | 70 |
| Irgacure 2959 | 0.5 | 0.5 | 0.5 | 0.5 | 0.5 | 0.5 |
| Direct Fast Red 3B | 5 | 5 | 5 | 5 | 5 | 5 |
| Stability of dissolution | ○ | ○ | ○ | ○ | ○ | ○ |
| Water resistance of cured material | ○ | ○ | ○ | ○ | ○ | ○ |

Comparative Examples 7 to 12

Each raw material was mixed in a formulation as shown in Table 10, and the reaction product was subjected to evaluations as in Examples 45 to 54. These results are summarized in Table 10.

TABLE 10

| | Comparative Examples | | | | | |
|---|---|---|---|---|---|---|
| | 7 | 8 | 9 | 10 | 11 | 12 |
| Polyethylen glycol diacrylate monomer | Monomer (1) | Monomer (1) | Monomer (1) | Monomer (2) | Monomer (2) | Monomer (2) |
| Addition level | 30 | 30 | 30 | 30 | 30 | 30 |
| Deionized water | 70 | 70 | 70 | 70 | 70 | 70 |
| Irgacure 2959 | 0.5 | 0.5 | 0.5 | 0.5 | 0.5 | 0.5 |
| Benzopurpurine 4B | 5 | — | — | 5 | — | — |
| Direct Fast Brown BX | — | 5 | — | — | 5 | — |
| Direct Fast Red 3B | — | — | 5 | — | — | 5 |
| Stability of dissolution | X | X | X | X | X | X |
| Water resistance of cured material | Δ | Δ | Δ | X | X | X |

The contents of Table 6 to 10 will be discussed below.

The units of numerical values in the tables are parts by mass, unless particularly indicated. VEEA: 2-(vinyloxyethoxy)ethyl acrylate; VEEM: 2-(vinyloxyethoxy)ethyl methacrylate; TEG: tetraethylene glycol; polyglycerin: Polyglycerin #750 (trademark, product of Sakamoto Yakuhin Kogyo Co., Ltd.); TMP-30EO: trimethylolpropane with 30 oxyethylene groups; Irgacure 2959: 1-[4-(2-hydroxyethoxy)-phenyl]-2-hydroxy-2-methyl-1-propane-1-on, water-soluble photo polymerization initiator (trademark, product of Ciba Specialty Chemicals); Benzopurpurine 4B: red direct dye, also called Direct Red 2; Direct Fast Brown BX: brown direct dye; Direct Fast Red 3B: red direct dye; monomer (1): diacrylate of polyethylene glycol (PEG) with a number average molecular weight of 400; monomer (2): diacrylate of PEG with a number average molecular weight of 1000

What is claimed is:

1. A process for producing a compound having a (meth)acryloyl group
   which comprises reacting a compound having both a (meth)acryloyl group and a vinyl ether group with a compound having at least two functional groups capable of an addition reaction with said vinyl ether group.

2. A compound having a (meth)acryloyl group
   which is obtained by an addition reaction of a functional group of a compound (A) having at least two functional groups and the vinyl ether group of a compound (B) having both a (meth)acryloyl group and a vinyl ether group,
   said functional groups of said compound (A) being selected from the group consisting of a hydroxyl group, a carboxyl group and a thiol group.

3. The compound having a (meth)acryloyl group according to claim 2,
   wherein the compound (A) being selected from the group consisting of an epoxy acrylate, an unsaturated polyester, a phenol resin, an epoxy resin, a phenoxy resin and a hydroxyl group-containing polymer.

4. A compound having a (meth)acryloyl group
   which has in a molecule at least two of (meth)acryloyl group-containing groups,
   said (meth)acryloyl group-containing groups being a group represented by the general formula (1):

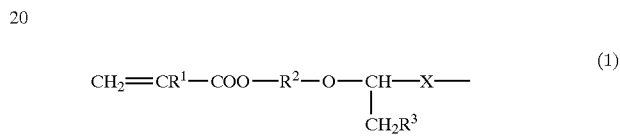

(1)

wherein $R^1$ represents a hydrogen atom or a methyl group, $R^2$ represents an organic moiety selected from the group consisting of linear, branched or cyclic alkylene group of 2 to 18 carbon atoms, an alkoxyalkylene group of 2 to 20 carbon atoms, a halogenated alkylene group of 2 to 8 carbon atoms, a polyethylene glycol structure except for the end hydroxyl groups, a polypropylene glycol structure except for the end hydroxyl groups, a polybutylene glycol structure except for the end hydroxyl groups and an aryl aroup, $R^3$ represents a hydrogen atom or an organic moiety, and X represents an oxygen or a sulfur atom, and/or a group represented by the general formula (2):

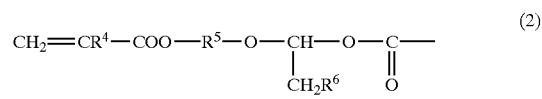

(2)

wherein $R^4$ represents a hydrogen atom or a methyl group, $R^5$ represents an organic moiety selected from the group consisting of a linear, branched or cyclic alkylene group of 2 to 18 carbon atoms, an alkoxyalkylene group of 2 to 20 carbon atoms, a halogenated alkylene group of 2 to 8 carbon atoms, a polyethylene glycol structure except for the end hydroxyl groups, a polypropylene glycol structure except for the end hydroxyl groups, a polybutylene glycol structure except for the end hydroxyl groups and an aryl group, $R^6$ represents a hydrogen atom or an organic moiety.

5. A photo-curable composition which comprises both the compound having a (meth)acryloyl group according to claim 2, and a photo polymerization initiator.

6. The photo-curable composition according to claim 5 which further comprises an inorganic powder.

7. An aqueous photo-curable composition which comprises the compound having a (meth)acryloyl group according to claim 2, and water.

8. A photo-curable composition which comprises both the compound having a (meth)acryloyl group according to claim 3, and a photo polymerization initiator.

9. A photo-curable composition which comprises both the compound having a (meth)acryloyl group according to claim 4, and a photo polymerization initiator.

10. The photo-curable composition according to claim 8, which further comprises an inorganic powder.

11. The photo-curable composition according to claim 9, which further comprises an inorganic powder.

12. An aqueous photo-curable composition which comprises the compound having a (meth)acryloyl group according to claim 3, and water.

13. An aqueous photo-curable composition which comprises the compound having a (meth)acryloyl group according to claim 4, and water.

14. The process for producing a compound having a (meth)acryloyl group according to claim 1,
wherein said process is performed in the presence of a polymerization inhibitor.

15. The compound having a (meth)acryloyl group according to claim 2, which further contains a carboxyl group.

16. The compound having a (meth)acryloyl group according to claim 2, which further contains a carboxyl group and has an acid value of 20 to 200 mg KOH/g.

17. The compound having a (meth)acryloyl group according to claim 3, which further contains a carboxyl group.

18. The compound having a (meth)acryloyl group according to claim 3, which further contains a carboxyl group and has an acid value of 20 to 200 mg KOH/g.

19. The compound having a (meth)acryloyl group according to claim 4, which further contains a carboxyl group.

20. The compound having a (meth)acryloyl group according to claim 4, which further contains a carboxyl group and has the acid value of 20 to 200 mg KOH/g.

* * * * *